United States Patent
Kieda et al.

(10) Patent No.: US 9,228,173 B2
(45) Date of Patent: Jan. 5, 2016

(54) ORGAN-SPECIFIC FELINE ENDOTHELIAL CELLS AND USES THEREOF

(75) Inventors: Claudine Kieda, Orleans (FR); Maria Paprocka, Wroclaw (PL); Michele Mitterand, Ardon (FR); Nathalie Lamerant-Fayel, Olivet (FR); Henri-Jean Boulouis, La Varenne Saint Hilaire (FR); Nadia Haddad, Saint-Maurice (FR); Martine Monteil, Villeneuve-Saint-Georges (FR)

(73) Assignees: CENTRE NATIONAL DE LA RECHERCHE SCIENTIFIQUE—CNRS, Paris (FR); ECOLE NATIONALE VETERINAIRE D'ALFORT, Maisons-Alfort (FR)

(*) Notice: Subject to any disclaimer, the term of this patent is extended or adjusted under 35 U.S.C. 154(b) by 0 days.

(21) Appl. No.: 13/521,423

(22) PCT Filed: Jan. 11, 2011

(86) PCT No.: PCT/FR2011/050037
§ 371 (c)(1),
(2), (4) Date: Oct. 4, 2012

(87) PCT Pub. No.: WO2011/083285
PCT Pub. Date: Jul. 14, 2011

(65) Prior Publication Data
US 2013/0017547 A1  Jan. 17, 2013

(30) Foreign Application Priority Data
Jan. 11, 2010 (FR) ...................................... 10 00094

(51) Int. Cl.
C12N 5/00 (2006.01)
C12N 5/071 (2010.01)
G01N 33/50 (2006.01)

(52) U.S. Cl.
CPC ............ *C12N 5/069* (2013.01); *G01N 33/5064* (2013.01)

(58) Field of Classification Search
None
See application file for complete search history.

(56) References Cited

U.S. PATENT DOCUMENTS

2004/0062756 A1* 4/2004 Humeau et al. ............ 424/93.21

OTHER PUBLICATIONS

Fletcher et al., Veterinary Immunology and Immunopathology, 2006, vol. 109, pp. 233-244.*
Steffan et al., Hepatology, 1996, vol. 23, pp. 964-970.*
Fletcher N F et al., "Growth and characterisation of a cell culture model of the feline blood-brain barrie", Veierinary Immunology and Immunopathology, Amsterdam, NL LNKD-DOI :10.1016/J.VETIMM.2005.08.025, vol. 109, No. 3-4, Feb. 15, 2006, pp. 233-244.
Steffan Anne-Marie et al., "Productive infection of primary cultures of endothelial cells from the cat liver sinusoid with the feline immunodeficiency virus", Hepatology, vol. 23, No. 5, 1996, pp. 964-970.
Proulx S et al., "Transplantation of a tissue-engineered corneal endothelium reconstructed on a devitalized carrier in the feline model", Investigative Ophthalmology and Visual Science 2009 Association for Research in Vision and Ophthalmology Inc., vol. 50, No. 6, 2009, pp. 2686-2694.
Luo W-J et al., "Cloning, expression and functional analyses of human platelet-derived growth factor-B chain peptide for wound repair of cat corneal endothelial cells", Chinese Journal of Traumatology—English Edition Feb. 1, 2009, vol. 12, No. 1, Feb. 1, 2009, pp. 31-37.
Breitschwerdt et al., "Feline bartonellosis and cat scratch disease", Veterinary Immunology and Immunopathology, vol. 123, No. 1-2, May 15, 2008, pp. 167-171.
Regnery, R.L., et al. "Characterization of a Novel *Rochalimaea* Species, *R. henselae* sp. nov., Isolated from Blood of a Febrile, Human Immunodeficiency Virus-Positive Patient". J Clin Microbioly, Feb. 1992, pp. 265-274.
Boulouis, H.J., et al. Persistent Bartonella Infection: Epidemiological and Clinical Implications. Bull Acad Natl Med, Jun. 2007, vol. 191, No. 6, pp. 1037-1049.
Koehler, J.E., et al., "Molecular Epidemiology of Bartonella Infections in Patients with Bacillary Angiomatosis-Peliosis". The New England Journal of Medicine, Dec. 25, 1997, 337:1876-1883.
Boulouis, H.J., et al. "Factors associated with the rapid emergence of zoonotic Bartonella infections". Vet Res, 2005, 36:383-410.
Yamamoto, K., et al. "Experimental infection of specific pathogen free (SPF) cats with two different strains of Bartonella henselae type I: a comparative study". Vet Res, 2002, 33:669-684.
Breitschwerdt, E.B., et al. "Feline bartonellosis and cat scratch disease". Vet Immunology and Immunopatholy, 2008, 123:167-71.
Bergmans, A.M., et al. "Predominance of Two *Bartonella henselae* Variants among Cat-Scratch Disease Patients in the Netherlands". Journal of Clinical Microbiology, Feb. 1996, 34:254-260.
Sander, A., et al. "Two Different Genotypes of Bartonella henselae in Children with Cat-Scratch Disease and their Pet Cats". Scand J Infect Dis, 1998, 30:387-391.
Sander, A., et al. "Detection of Bartonella henselae DNA by Two Different PCR Assays and Determination of the Genotypes of Strains Involved in Histologically Defined Cat Scratch Disease". Journal Clinical Microbiology, Apr. 1999, 37:993-997.

(Continued)

*Primary Examiner* — Michele K Joike
*Assistant Examiner* — Mindy G Brown
(74) *Attorney, Agent, or Firm* — Arent Fox LLP

(57) ABSTRACT

The present invention relates to isolated organ-specific feline endothelial cells. Specifically, the present invention relates to established organ-specific feline endothelial cells. The present invention also relates to organ-specific feline endothelial cells derived from micro- and macro-vascularisation. The present invention also relates to methods for screening molecules, for studying pathologies and for producing pathogens using same.

3 Claims, 6 Drawing Sheets

(56) References Cited

OTHER PUBLICATIONS

Fournier, P.E., et al. "Improved Culture from Lymph Nodes of Patients with Cat Scratch Disease and Genotypic Characterization of *Bartonella henselae* Isolates in Australia". Journal of Clinical Microbiology, Oct. 2002, 40:3620-3624.

Dillon, B., et al. "Limited Diversity among Human Isolates of *Bartonella henselae*". Journal of Clinical Microbiology, Dec. 2002, 40:4691-4699.

Woestyn, S., et al. "Study of Genotypes and virB4 Secretion Gene of *Bartonella henselae* strains from Patients with Clinically Definied Cat Scratch Disease". Journal of Clinical Microbiology, Apr. 2004, 42:1420-1427.

Bouchouicha, R., et al. "Molecular Epidemiology of Feline and Human *Bartonella henselae* Isolates". Emerging Infectious Diseases, May 2009, 15: 813-816.

Leboit, P.E., et al. "Bacillary Angiomatosis: The Histopathology and Differential Diagnosis of a Pseudoneoplastic Infection in Patients with Human Immunodeficiency Virus Disease". The American Journal of Surgical Pathology, 1989, 13:909-920.

Batterman, H.J., et al. "*Bartonella henselae* and *Bartonella quintana* Adherence to and Entry into Cultured Human Epithelial Cells". Infection and Immunity, Nov. 1995, 63:4553-4556.

Riess, T., et al. "Analysis of *Bartonella* Adhesin A Expression Reveals Differences between Various *B. henselae* Strains". Infection and Immunity, Jan. 2007, 75:35-43.

Riess, T., et al. "*Bartonella* Adhesin A Mediates a Proangiogenic Host Cell Response". J. Exp. Med, Nov. 15, 2004, 200:1267-1278.

Conley, T., et al. "*Rochalimaea* species stimulate human endothelial cell proliferation and migration in vitro". J Lab Clin Med, Oct. 1994, 124:521-528.

Palmari, J., et al. "Image cytometry and topographical analysis of proliferation of endothelial cells in vitro during *Bartonella* (*Rochalimaea*) infection". Analytical Cellular Pathology, 1996, 11:13-30.

Maeno, N. H., et al.: "Live *Bartonella henselae* enhances endothelial cell proliferation without direct contact". Microbial Pathogenesis, 1999, 27:419-427.

Mccord, A.M., et al. "*Bartonella*-Induced Endothelial Cell Proliferation is Mediated by Release of Calcium from Intracellular Stores". DNA and Cell Biology, 2007, 26:657-664.

Mccord, A.M., et al. "Interaction of *Bartonella henselae* with Endothelial Cells Promotes Monocyte/macrophage Chemoattractant Protein 1 Gene Expression and Protein Production and Triggers Monocyte Migration". Infection and Immunity, Sep. 2005, 73:5735-5742.

Kempf. V.A., et al. "Evidence of a leading role for VEGF in *Bartonella henselae*-induced endothelial cell proliferations". Cellular Microbiology, 2001, 3(9):623-632.

Resto-Ruiz, S.I., et al. "Induction of a Potential Paracrine Angiogenic Loop between Human THP-1 Macrophages and Human Microvascular Endothelial Cells during *Bartonella henselae* Infection". Infection and Immunity, Aug. 2002, 70:4564-4570.

Ferrara, N., et al. "The biology of VEGF and its receptors". Nature Medicine, Jun. 2003, 9(6):669-678.

Schmid, M.C., et al. "A Translocated Bacterial Protein Protects Vascular Endothelial Cells from Apoptosis". PLoS Pathogens, Nov. 2006, 2(11):1083-1097.

Bizouarne, N., et al. "A SV-40 immortalized murine endothelial cell line from peripheral lymph node high endothelium expresses a new $\alpha$-L-fucose binding protein". Biol Cell 1993, 79:209-218.

Bizouarne, N., et al. "Characterization of membrane sugar-specific receptors in cultured high endothelial cells from mouse peripheral lymph nodes". Biol Cell 1993, 79:27-35.

Kieda, C., et al. "New Human Microvascular Endothelial Cell Lines with Specific Adhesion Molecules Phenotypes". Endothelium 2002, 9:247-261.

Gurfield, A.N., et al. "Epidemiology of *Bartonella* infection in domestic cats in France". Veterinary Microbiology, 2001, 80:185-98.

Steffan, A., et al. "Productive Infection of Primary Cultures of Endothelial Cells From the Cat Liver Sinusoid With the Feline Immunodeficiency Virus". Hepatology, May 1996, 23(5):964-970.

Proulx, S., et al. "Transplantation of a Tissue-Engineered Corneal Endothelium Reconstructed on a Devitalized Carrier in the Feline Model". Investigative Ophthalmology and Visual Science, Jun. 2009, 50(6):2686-2694.

Luo, W., et al: "Cloning, expression and functional analyses of human platelet-derived growth factor-B chain peptide for wound repair of cat corneal endothelial cells". Chinese Journal of Traumatology, 2009, 12(1):31-37.

Fletcher, N. et al: Growth and characterisation of a cell culture model of the feline blood-brain barrier. Vet Immunol Immunopathol. Feb. 15, 2006; 109(3-4):233-44.

\* cited by examiner

ORGAN-SPECIFIC FELINE ENDOTHELIAL CELLS AND USES THEREOF

CROSS-REFERENCE TO RELATED APPLICATION

This Application is a National Stage entry of International Application No. PCT/FR2011/050037, having an international filing date of Jan. 11, 2011; which claims priority to French Application No.: 1000094, filed Jan. 11, 2010; the disclosure of each of which is hereby incorporated in its entirety by reference.

FIELD OF TECHNOLOGY

The present invention relates to isolated organ-specific feline endothelial cells. The present invention also relates to methods for screening molecules, for studying pathologies and for producing pathogens using same.

The present invention finds applications notably in the medical and veterinary area, in particular in the area of therapeutics, in the area of investigation of cellular mechanisms, in the area of research into new therapeutic molecules and/or in the area of investigation of microorganisms.

In the following description, the references in square brackets ([ ]) refer to the list of references given at the end of the text.

PRIOR ART

It is known in the prior art that microorganisms that cause pathologies, such as bacteria, viruses etc., can be transmitted from one mammal to another, including humans.

For example, since its discovery in 1992, in the article Regnery R L, Anderson B E, Clarridge J E, Rodriguez-Barradas M C, Jones D C, Carr J H: Characterization of a novel *Rochalimaea* species, *R. henselae* sp. nov., isolated from blood of a febrile, human immunodeficiency virus-positive patient. J Clin Microbiol 1992, 30:265-274[1] *Bartonella henselae* is considered to be mainly responsible for benign inoculation lymphoreticulosis in humans as described in Boulouis H J, Haddad N, Vayssier-Taussat M, Maillard R, Chomel B: Persistent *Bartonella* infection: epidemiological and clinical implications. Bull Acad Natl Med 2007, 191: 1037-10 1044 [2]. This intracellular bacterium is responsible for more serious forms of the disease in immunodepressed patients, such as bacillary angiomatosis (BA) and bacillary peliosis (BP), characterized by pseudotumoral proliferation of the endothelial cells of small blood vessels. These rare vascular lesions are produced mainly or exclusively in the skin, the liver and the spleen as described in Koehler J E, Sanchez M A, Garrido C S, Whitfeld M J, Chen F M, Berger T G, Rodriguez-Barradas M C, Leboit P E, Tappero J W: Molecular epidemiology of *Bartonella* infections in patients with bacillary angiomatosis-peliosis. N Engl J Med 1997, 337:1876-1883[3]. It was stated in Boulouis H J, Chang C C, Henn J B Kasten R W, Chomel B B: Factors associated with the rapid emergence of zoonitic *Bartonella* infections. Vet Res 2005, 36:338-410 [4] that cats are the principal reservoir of this zoonitic bacterium. Immunocompetent or immunodepressed cats, infected either naturally or experimentally, usually show no clinical sign of infection, as was described by Yamamoto K, Chomel B B, Kasten R W, Hew C M, Weber D K, Lee W I: Experimental infection of specific pathogen free (SPF) cats with two different strains of *Bartonella henselae* type I: a comparative study. Vet Res 2002, 3:669-684 [5] and Breitschwerdt E B: Feline bartonellosis and cat scratch disease. Vet Immunol Immunopathol 2008, 123:167-71 [6].

Two genotypes (I and II) of *B. henselae* were described in Bergmans A M, Schellekens J, van Embden J, Schouls L M: Predominance 1 of two *Bartonella henselae* variants among cat-scratch disease patients in the Netherlands. J Clin Microbiol 1996, 34:254-260 [7] based on analysis of the rRNA 16S sequences. Epidemiological studies strongly suggest that genotype I would be more virulent in humans than genotype II, as described in Bergmans A M et al. [7]; Sander A, Ruess M, Deichmann K: Two different genotypes of *Bartonella henselae* in children with cat-scratch disease and their pet cats. Scand J Infect Dis 1998, 30:387-391 [8]; Sander A, Posselt M, Bohm N, Ruess M, Altwegg M: Detection of *Bartonella henselae* DNA by two different PCR assays and determination of the genotypes of strains involved in histologically defined cat scratch disease. J Clin Microbiol 1999, 37:993-997 [9]; Fournier P E, Robson J, Zeaiter Z, Mc Dougall R, Byrne S, Raoult D: Improved culture from lymph nodes of patients with cat scratch disease and genotypic characterization of *Bartonella henselae* isolates in Australia. J Clin Microbiol 2002, 40:3620-3624 [10];

Dillon B, Valenzuela J, Don R, Blanckenberg D, Wigney D I, Malik R, Morris A J, Robson J M, Iredell J: Limited diversity among human isolates of *Bartonella henselae*. J Clin Microbiol 2002, 40:4691-4699 [11]; Woestyn S, Olivé N, Bigaignon G, Avesani V, Delmée M: Study of genotypes and virB4 secretion gene of *Bartonella henselae* strains from patients with clinically defined cat scratch disease. J Clin Microbiol 2004, 42:1420-1427 [12] and Bouchouicha R, Durand B, Monteil M, Chomel B, Berrich M, Birtles R, Breitschwerdt E, Koehler J, Kasten R, Petit E, Maruyama S, Arvand M, Boulouis H-J, Haddad N: Epidemiological applications of Multi-locus Variable number tandem 1 repeat Analysis (MLVA) for *Bartonella henselae* of Human and Feline origins. Emerg Infect Dis 2009, 15: 813-816 [13]). To date, no experimental study has confirmed this hypothesis.

The presence of micro-colonies of *Bartonella* adjacent to proliferating endothelial cells was demonstrated histologically in LeBoit P E, Berger T G, Egbert B M, Beckstead J H, Yen T S B, Stoler M H: Bacillary angiomatosis: The histopathology and differential diagnosis of a pseudoneoplastic infection in patients with human immunodeficiency virus disease. Am J Surg Pathol 1989, 13:909-920 [14], indicating that *Bartonella*-endothelial cells (ECs) interactions might be involved in the proangiogenic process, leading to vascular lesions.

Approaches based on culturing primary endothelial cells derived from the macrovascularization obtained from the human umbilical vein (HUVEC: Human Umbilical Vein Endothelial Cells) were used for identifying the virulence factors of *B. henselae*. Adhesin A (BadA) from *Bartonella*, originally described as "pilus" in Batterman H J, Peek J A, Loutit J S, Falkow S, Tompkins L S: *Bartonella henselae* and *Bartonella quintana* adherence to and entry into cultured human epithelial cells. Infect Immun 1995, 63:4553-4556 [15] is important for pathogenicity, as indicated in the scientific work Riess T, Raddatz G, Linke D, Schäfer A, Kempf V A J: Analysis of *Bartonella* adhesin A expression reveals differences between various *B. henselae* strains. Infect Immun 2007, 75:35-43 [16]. In fact, BadA is involved in adhesion to the proteins of the extracellular matrix and to ECs, during activation of hypoxia-inducible factor 1 (Hypoxy Inducible factor 1/HIF1) and during secretion of proangiogenic cytokines as described in Riess T, Andersson S G, Lupas A, Schaller M, Schäfer A, Kyme P, Martin J, Wälzlein J H, Ehehalt U, Lindroos H, Schirle M, Nordheim A, Autenrieth I B, Kempf V A: *Bartonella* adhesin A mediates a proangiogenic host cell response. J Exp Med 2004, 200:1267-1278 [17].

Other studies have suggested that the process by which *B. henselae* might induce proliferation of endothelial cells (ECs) very probably involves the release of bacterial factors as noted in Conley T, Slater L, Hamilton K: *Rochalimaea* species stimulate human endothelial cell proliferation and migration in vitro. J Lab Clin Med 1994, 124:521-528 [18]; Palmari J, Teysseire N, Dussert C, Raoult D: Image cytology and topographical 1 analysis of proliferation of endothelial cells in vitro during *Bartonella* (Rochalimaea) infection. Analytical Cell Pathol 1996, 11:13-30 [19]; Maeno N H, Oda K, Yoshiie M R, Wahid T F, Matayoshi S: Live *Bartonella henselae* enhances endothelial cell proliferation without direct contact. Microb Pathog 1999, 7 27:419-427 [20]; McCord A M, Cuevas J, Anderson B E: *Bartonella*-induced endothelial cell proliferation is mediated by release of calcium from intracellular stores. DNA Cell Biol 2007, 26:657-11 663 [21].

It has also been shown that factors from the host play a role in vitro in the *B. henselae*-host interactions leading to angiogenesis. According to McCord A M, Burgess A W O, Whaley M J, Anderson B E: Interaction of *Bartonella henselae* with endothelial cells promotes monocyte/macrophage chemoattractant protein 1 gene expression and protein production and triggers monocyte migration. Infect Immun 2005, 73:5735-5742 [22], infected endothelial cells can induce the expression and production of proangiogenic proteins. Studies of the expression of vascular endothelial growth factor (VEGF) in clinical samples described in Kempf V A, Volkmann B, Schaller M: Evidence of a leading role for VEGF in *Bartonella henselae*-induced endothelial cell proliferations. Cell Microbiol 2001, 3:623-632 [23] or in cultures of endothelial cells (ECs) as described in Maneo et al. [20], Kempf et al. [23] and Resto-Ruiz S I, Schmiederer M, Sweger D, Newton C, Klein T W, Friedman H, Anderson B E: Induction of a potential paracrine angiogenic loop between human THP-1 macrophages and human microvascular endothelial cells during *Bartonella henselae* infection. Infect Immun 2002, 70:4564-4570 [24] suggest in fact exogenous production of VEGF, and involvement of increased expression of VEGF receptors, in particular VEGFR-2, by ECs as described in Ferrara N, Gerber H P, Le Couter J: The biology of VEGF and its receptors. Nature Medicine 2003, 9:669-676 [25]. Moreover, the anti-apoptotic activity of the BepA molecule of *B. henselae*, a molecule associated with the type IV secretion system, in endothelial cells of the human umbilical vein is correlated with a large increase in the level of cyclic adenosine 3',5'-monophosphate (cAMP). Schmid M C, Scheidegger F, Dehio M, Balmelle-Devaux N, Schulein R, Guye P, Chennakesava C S, Biedermann B, Dehio C: A translocated bacterial protein protects vascular endothelial cells from apoptosis. PLoS Pathog 2006, 2:1083-1096 [26]

However, these studies are based exclusively on the use of HUVECs derived from the macrovascularization. These cells are very different from the ECs derived from the microvascularization involved in the aforementioned disorders.

There is therefore a real need to isolate, to characterize and to be able to use isolated endothelial cells from the microvascularization.

There is therefore a real need to find endothelial cells that are involved in these processes so as to be able to study the cellular mechanisms, for example the mechanisms of interactions between *B. henselae* and the vascular endothelium.

Moreover, the cells used in the prior art are human cells, which do not show why microorganisms that are not pathogenic for cats, for example, are for humans. At present there are no established cell lines of feline endothelial cells.

There is therefore a real need to isolate, to characterize and to be able to use isolated endothelial cells in order to study the cellular and molecular mechanisms involved in the colonization of these cells by microorganisms and/or identify the elements of the cell that promote and/or inhibit the development of these microorganisms.

There is also a real need to isolate, to characterize and to be able to use isolated endothelial cells in order to study the cellular and molecular mechanisms involved in the colonization of these cells by microorganisms.

Moreover, in the prior art there are no comparative studies of the interaction between microorganisms, for example *B. henselae* and human endothelial cells or feline endothelial cells, knowing that microorganisms, such as *B. henselae*, can be zoonotic.

There is therefore a real need to isolate and to identify feline endothelial cells in order to be able to compare the mechanisms of interactions involved between feline endothelial cells and microorganisms and between human endothelial cells and microorganisms.

Moreover, there is, in the state of the art, a real need to isolate and to identify endothelial cells for screening molecules in order to identify those that are able to inhibit, stop and/or destroy the pathogenic microorganisms that are specific or nonspecific for endothelial cells.

Finally, there is a real need in the state of the art to isolate and identify endothelial cells for cultivating microorganisms, for example zoonotic microorganisms.

Moreover, it is also known in the prior art that microorganisms are specific to certain cells and to certain mammals. For example, the epicellular hemoparasite *Haemobartonella felis*, currently *Mycoplasma haemofelis* and *Mycoplasma haemominutum*, which causes the disease called feline infectious anemia, is recognized as being one of the commonest causes of hemolytic anemias in domestic cats. However, in the state of the art there are still many unanswered questions concerning its manner of transmission, its prevalence and its clinical impact on domestic cat populations. Another problem in the state of the art is to find efficient means for identifying these microorganisms.

There is therefore a real need to isolate and to identify feline endothelial cells in order to be able to study the microorganisms that are specific to these cells and/or identify therapeutic molecules for treating disorders associated with these microorganisms and/or for inhibiting and/or destroying these microorganisms.

DESCRIPTION OF THE INVENTION

Thus, the present invention makes it possible to solve the aforementioned problems and drawbacks of the prior art, by supplying organ-specific feline endothelial cells.

The present invention also relates to feline endothelial cells of the macrovascularization and of the microvascularization and their characterization as endothelial cells.

The inventors are the very first to have succeeded in isolating and establishing cell lines of organ-specific feline endothelial cells.

Moreover, the inventors have immortalized said cells and have obtained established cell lines, i.e. immortalized cell lines that are stable, nontumorigenic and have characteristics that are identical from one generation to the next. A definition of an established cell line is given in the book Gene IV, by Benjamin Leuvine, page 1133, 6th edition, De Boeck University.

The present invention therefore relates to an isolated organ-specific feline endothelial cell comprising the Von Willebrand factor, the angiotensin converting enzyme and the clusters of differentiation (CD) CD 31, 34, 105, 54, 62E, 62P, 146.

The present invention also relates to a set of isolated organ-specific feline endothelial cells comprising the Von Willebrand factor, the angiotensin converting enzyme and the clusters of differentiation (CD) CD 31, 34, 105, 54, 62E, 62P, 146.

Examples of isolated organ-specific feline endothelial cells according to the present invention were deposited at the National Collection of Cultures of Microorganisms (Collection Nationale de Culture de Microorganismes, CNCM), Institut Pasteur, 25 rue du Docteur Roux, 75724 PARIS Cedex 15, on Nov. 24, 2009, under the CNCM numbers No. I-4250 (F Int MEC), No. I-4251 (F PLN MEC), No. I-4252 (F Om EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

In the present, "organ-specific" means cells representing the microvascularization or the macrovascularization of each of the organs from which they are derived.

The inventors have demonstrated that the endothelial cells differ depending on the tissue origin, and are the key to the specificity of targeting an organ or tissue by controlling the molecular and cellular mechanisms that govern, for example, entry into the tissue beneath the endothelial wall. The inventors also demonstrated that the endothelial cells of the microvascularization are distinct and therefore have a molecular and biological behavior different from the endothelial cells of the macrovascularization.

The present invention also relates to isolated organ-specific feline endothelial cells derived from the microvascularization. Examples of isolated organ-specific feline endothelial cells derived from the microvascularization according to the invention were deposited at the Collection Nationale de Culture de Microorganismes (CNCM), Institut Pasteur, 25 rue du Docteur Roux, 75724 PARIS Cedex 15, on Nov. 24, 2009 under the CNCM numbers No. I-4250 (F Int MEC), No. I-4251 (F PLN MEC), No. I-4252 (F Om EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

The present invention also relates to isolated organ-specific feline endothelial cells derived from the macrovascularization. Examples of isolated organ-specific feline endothelial cells derived from the macrovascularization according to the invention were deposited at the Collection Nationale de Culture de Microorganismes (CNCM), Institut Pasteur, 25 rue du Docteur Roux, 75724 PARIS Cedex 15, on Nov. 24, 2009 under the CNCM numbers No. I-4250 (F Int MEC), No. I-4251 (F PLN MEC), No. I-4252 (F Om EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

The present invention also relates to the cell cultures comprising the cells of the present invention.

The inventors also demonstrated that incubation of the cells of the invention with particular compounds, for example angiogenesis stimulating factors, allowed the proliferation and development of a vascular tissue.

The invention therefore also relates to a method for screening molecules that are able to induce differentiation and/or specialization of a feline endothelial cell comprising the following steps:

introducing at least one molecule to be screened into a medium suitable for culture of said cell, introducing at least one isolated feline endothelial cell according to the invention into said medium, culturing said cells in said medium for a sufficient time to permit differentiation and/or specialization of said cells, taking at least one cultured cell from said culture medium, observing the differentiation and/or specialization of said cell by phenotypic observation of the cell and/or by detecting differentiation markers.

Preferably, in the method for screening molecules, the feline endothelial cell is an isolated organ-specific feline endothelial cell comprising the Von Willebrand factor, the angiotensin converting enzyme and the clusters of differentiation (CD) CD 31, 34, 105, 54, 62E, 62P, 146. More preferably, the feline endothelial cell is selected from the group comprising the cells deposited at the Collection Nationale de Culture de Microorganismes (CNCM), Institut Pasteur, 25 rue du Docteur Roux, 75724 PARIS Cedex 15, on Nov. 24, 2009 under the CNCM numbers No. I-4250 (F Int MEC), No. I-4251 (F PLN MEC), No. I-4252 (F Om EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

The "molecule to be screened" can be for example a chemical molecule, a peptide, a hormone, a nucleic acid molecule, a plant extract. For example, the molecule to be screened can be a molecule that is commercially available and/or for which we wish to know its effect on the cells of the present invention, for example vascular endothelial growth factor (VEGF), vascular permeability factor (VPF), members of the epidermal growth factor (EGF) family.

They can also be molecules known by a person skilled in the art that are able to induce, or inhibit angiogenesis. For example, they can be molecules selected from the group comprising VEGF, angiopoietins-1 and 2.

According to the present invention, the "suitable culture medium" can be any culture medium known by a person skilled in the art suitable for the culture of feline endothelial cells. It can be for example a commercially available culture medium. It can be for example a culture medium described in Bizouarne N, Denis V, Legrand A, Monsigny M, Kieda C: A SV-40 immortalized murine endothelial cell line from peripheral lymph node high endothelium expresses a new alpha-l-fucose binding protein. Biol Cell 1993, 79:209-218 [27], media marketed by the company Promocell, the DMEM medium (registered trademark), DMEM/F-12 (registered trademark), F-10 (registered trademark), F-12 (registered trademark), MEM (registered trademark), RPMI (registered trademark), OptiMEM (brand name) marketed by the company Invitrogen.

According to the invention, the culture medium can in addition be supplemented with a fungicide, for example fongizone (brand name); an antibiotic, for example gentamicin (brand name); fetal calf serum. A person skilled in the art will easily be able to adapt the culture medium, on the basis of his general knowledge.

According to the invention, the feline endothelial cells can be cultured at a temperature for example between 5° C. and 45° C., preferably at a temperature between 17 and 40° C., preferably at a temperature of 37° C.

According to the invention, the feline endothelial cells can be cultured in an atmosphere comprising a $CO_2$ percentage between 2 and 10%, preferably between 4 and 6%, even more preferably of 5%.

According to the invention, the feline endothelial cells can be cultured in a humid atmosphere, for example an atmosphere with a humidity level between 50 and 90%, preferably between 60 and 85%.

According to the invention, differentiation markers can be detected by any means and/or method known by a person skilled in the art. For example, it can be the use of specific antibodies of said markers or other means known by a person skilled in the art. For example, they can be commercially available antibodies, antibodies capable of cross-reacting with the cat, for example they can be antibodies described in the work of Fletcher N. F. et al. (2006) [31] and Kieda C. et al., (2002) [29], for example commercially available antibodies, for example monoclonal antibodies, for example mouse monoclonal antibodies (anti-CD49e or anti-CD29) marketed by the company Serotec, the company Sigma, the company Becton Dickinson Biosciences, polyclonal antibodies (rabbit anti-Von Willebrand factor antibodies Dako, Cambridge UK-).

In the present, cell culture can take place in any container known by a person skilled in the art, for example Petri dishes, 6-well, 24-well, 96-well plates, test tubes.

In the present, the sampling step can be carried out by any method known by a person skilled in the art. For example, sampling can be performed by a sampling device, for example a ClonePix or ClonePixFL robot marketed by the company PROTEIGENE, a sampling tube intended for analysis by cytofluorometry.

In the present, the phenotypic observation can be performed by any method known by a person skilled in the art. For example, it can be performed by direct observation, by observation with a microscope, for example an optical microscope, a scanning electron microscope. It can be for example a Zeiss axiovert 200M video microscope (registered trademark), a Nikon TMS microscope (registered trademark).

The present invention also relates to a kit for carrying out the method of the present invention comprising at least one isolated feline endothelial cell of the present invention and a means for detecting cellular differentiation and/or specialization.

Advantageously, the endothelial cells of the invention can be used for studying cellular and/or molecular mechanisms of infection of a cell by a microorganism.

Thus, the present invention also relates to a method for in vitro investigation of disorders due to a pathogenic microorganism comprising the following steps:
  culturing at least one feline endothelial cell according to the invention in a suitable culture medium,
  inoculating said cell with a pathogenic microorganism,
  culturing the inoculated cells, and
  observing one or more of the following criteria: development of the phenotype of the cells, development of cytotoxicity, induction of apoptosis, stimulation of growth of angiogenesis.

In the present invention, "microorganism" means bacteria, viruses, fungi, yeasts and protozoa.

In the method for studying disorders in vitro, the pathogenic microorganism can be a pathogenic microorganism specific or nonspecific for feline endothelial cells. For example, they can be microorganisms that are pathogenic for human cells, microorganisms pathogenic for human and feline cells and microorganisms that are only pathogenic for feline cells. It can be a microorganism specific for feline microvascular endothelial cells and/or a microorganism specific for feline macrovascular endothelial cells or nonspecific, and/or a microorganism that is nonspecific for feline endothelial cells.

It can be for example a microorganism specific for feline endothelial cells selected from the group comprising *Bartonella henselae, Mycoplasma haemofelis, Mycoplasma haemominutum, Anaplasma phagocytophilum* and *Rickettsia felis*.

Preferably, in the in vitro method for studying disorders, the feline endothelial cell is an isolated organ-specific feline endothelial cell comprising the Von Willebrand factor, the angiotensin converting enzyme and the clusters of differentiation (CD) CD 31, 34, 105, 54, 62E, 62P, 146. Even more preferably, the feline endothelial cell is selected from the group comprising the cells deposited at the Collection Nationale de Culture de Microorganismes (CNCM), Institut Pasteur, 25 rue du Docteur Roux, 75724 PARIS Cedex 15, on Nov. 24, 2009 under the CNCM numbers No. I-4250 (F Int MEC), No. I-4251 (F PLN MEC), No. I-4252 (F Om EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

In the present invention, cytotoxicity means an alteration of the cells, for example a genomic or physical alteration and/or any cellular alteration known by a person skilled in the art.

In the present invention, apoptosis means programmed cell death, i.e. the triggering of cellular mechanisms leading to death of the cell.

In the present invention, the observation step can be carried out by any method and/or means known by a person skilled in the art, for example by the methods described above. A person skilled in the art will, based on his general knowledge, easily be able to select and adapt, if necessary, the methods and/or means known in the prior art for carrying out this step. For example, observation of induction of apoptosis can be performed by imaging of cell death using a microscope, by detection of molecules involved in apoptotic processes in the culture medium, for example by means of specific antibodies, or by observation of nuclear condensation by Hoescht/DAPI staining. Observation of the stimulation of angiogenic growth can be performed, for example, by imaging of vascular structures with a microscope, by detecting molecules and/or specific markers of angiogenesis for example with specific antibodies.

Advantageously, the method for studying disorders in vitro also makes it possible to determine the pathogenicity of the microorganism with respect to the endothelial cell. If the microorganism is pathogenic, the growth of the endothelial cell is altered for example cell death or increase in cell lifetime), if the microorganism is not pathogenic, it has no effect on the cell.

Advantageously, the method of the invention also makes it possible to study the specificity and the targeting of a pathogen with respect to a category of endothelial cell, namely an endothelial cell of the micro- or macrovascularization. Thus, the present invention therefore advantageously also makes it possible to identify pathogenic microorganisms specific for microvascular or macrovascular endothelial cells.

The inventors have also demonstrated that the cells of the present invention can be used in methods for screening molecules that may have an action on a microorganism that is pathogenic with respect to a feline endothelial cell.

The invention therefore also relates to a method for screening molecules that may have an action on a microorganism that is pathogenic with respect to a feline endothelial cell comprising the following steps:
  introducing at least one molecule to be screened into a medium suitable for culture of said cell,
  introducing at least one feline endothelial cell into said medium,
  introducing the pathogenic microorganism into said medium, culturing the inoculated cells, and
observing the development or non-development of the microorganism.

In the method of the invention, the feline endothelial cell can be an isolated organ-specific feline endothelial cell comprising the Von Willebrand factor, the angiotensin converting enzyme and the clusters of differentiation (CD) CD 31, 34, 105, 54, 62E, 62P, 146, even more preferably, the feline endothelial cell is selected from the group comprising the cells deposited at the Collection Nationale de Culture de Microorganismes (CNCM), Institut Pasteur, 25 rue du Docteur Roux, 75724 PARIS Cedex 15, on Nov. 24, 2009 under the CNCM numbers No. I-4250 (F Int MEC), No. I-4251 (F PLN MEC), No. I-4252 (F Om EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

In the method for screening molecules, the microorganism can be a microorganism as defined above.

Advantageously, the method of the invention makes it possible to identify the molecules that are active on the microorganism before infection and/or the molecules that are active on the microorganism having an effect on the mechanism of infection of the cell by the microorganism.

In another embodiment of the method of the invention, the step of introducing the molecule to be screened can be carried out after the inoculation step. Thus, the method of the invention advantageously makes it possible to identify molecules that may be active on the microorganism, in the cell or on its surface, after infection.

The present invention also relates to a kit for carrying out the method of production of pathogenic microorganisms comprising at least one isolated feline endothelial cell of the invention and a means for inoculating said cell with said microorganism.

Moreover, the inventors have also demonstrated that endothelial cells from different species, feline or human, have different behavior with respect to pathogens. The inventors are the very first to have developed feline endothelial cell lines and to have demonstrated the effects in vitro of infection with strains of *Bartonella* (*B. henselae* genotype I/II and *B. tribocorum*) that are different in humans versus cats.

The inventors have also demonstrated that the use of the cells of the invention in a method for studying microorganisms advantageously makes it possible to identify pathogenic microorganisms specific for feline endothelial cells. The inventors have further demonstrated that microorganisms have different biological effects for feline endothelial cells than those observed with respect to human endothelial cells.

Thus, the cells of the present invention can be used in comparative studies of infection between endothelial cells other than feline cells, for example human endothelial cells, and cells of the invention by a microorganism in order to demonstrate, for example, the differences in pathogenicity of the microorganism from one cell to another.

Advantageously, the method of studying microorganisms according to the invention also makes it possible to investigate the specificity and targeting of one endothelial type relative to another in terms of vascular characteristics, i.e. according to whether the endothelial cells are cells of the micro- or macrovascularization.

The inventors have also demonstrated that the feline endothelial cells of the invention can be used as a reservoir and/or as a means for producing microorganisms, for example microorganisms dependent on feline endothelial cells.

The present invention therefore also relates to a method for in-vitro production of pathogenic microorganisms comprising the following steps:
culturing at least one feline endothelial cell of the invention in a suitable culture medium,
inoculating said cultured cell with said pathogenic microorganism,
culturing the inoculated cells permitting proliferation of said pathogenic microorganism, and
recovery of the pathogenic microorganisms produced.

In the present invention, the step of recovery of the microorganisms produced can be carried out by any technique and/or means known by a person skilled in the art.

Moreover, the cells of the present invention can be used in all the methods known in the prior art using cell cultures and/or cells.

The cells of the present invention find applications in the veterinary and medical fields, for example for identifying new therapeutic molecules, for studying pathogenic microorganisms, and for identifying specific pathogenic microorganisms.

For example, the cells of the present invention can be used in order to investigate, for example, the differential expression of factors that are indicative of disorders. Moreover, the cells of the invention can be used for studying effects in relation, for example, to tissue origin, i.e. for example whether endothelial cells are cells of the micro- or macrovascularization, and/or, for example, for comparing the results obtained with feline endothelial cells and those observed with respect to other species, for example human cells.

Moreover, the cells of the invention can be used, for example, in tests of inflammations and/or tests evaluating the possible effects of anti-inflammatory compounds depending on whether the endothelial cells are cells of the micro- or macrovascularization and/or, for example, for comparing the results obtained with feline endothelial cells and those observed with respect to endothelial cells of other species, for example human cells.

Other advantages may also occur to a person skilled in the art on reading the following examples, illustrated by the accompanying figures, given for purposes of illustration.

EXAMPLES

Example 1

Figure 1:
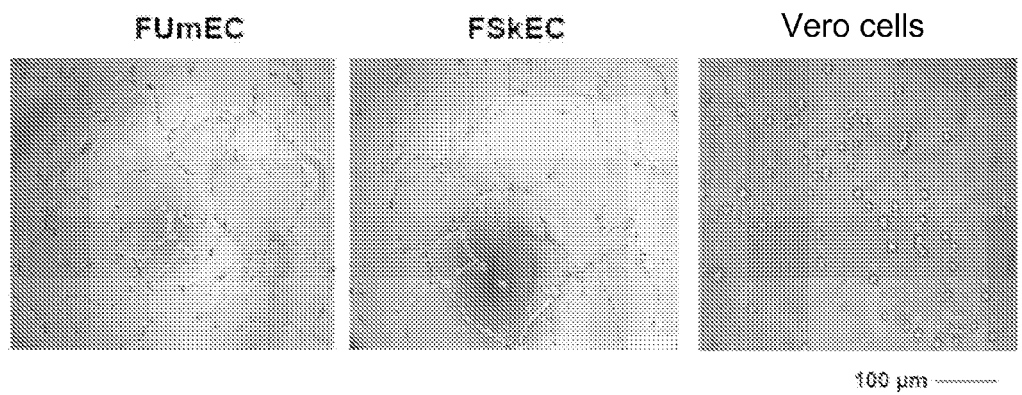
FIG. 1 shows photographs of angiogenesis of feline endothelial cells of the invention 10 hours after starting culture. FUcEC corresponds to the cell line of feline endothelial cells of the macrovascularization, FSkEC corresponds to the line of feline endothelial cells of the microvascularization, "Vero cells" corresponds to the control cells.

Isolation and Characterization of Feline Endothelial Cells

A. Materials and Methods
A.1. Samples Used

Four nonviable, immature embryos were removed aseptically by caesarean section from a mother after 45 days of gestation and 9 biopsies of organs or tissues were taken from each embryo. All the tissues and organs were put in RPMI medium (brand name) marketed by the company Gibco, BRL, Cergy-Pontoise France without fetal bovine serum and supplemented with antibiotics (penicillin and streptomycin) and stored at 4° C.

A.2. Isolation and Culture of the Cell Lines of Feline Endothelial Cells

Endothelial cells were isolated from the macrovascularization, i.e. from the umbilical cord or from the microvascularization, i.e. from the skin, lymph nodes, spleen, brain, liver, intestine and Peyer's patches according to the methods described in Bizouarne N, Denis V, Legrand A, Monsigny M, Kieda C: A SV-40 immortalized murine endothelial cell line from peripheral lymph node high endothelium expresses a new alpha-l-fucose binding protein. Biol Cell 1993, 79:209-218 [27]; and in Bizouarne N, Mitterrand M, Monsigny M, Kieda C: Characterization of membrane sugar specific receptors in cultured high endothelial cells from mouse peripheral lymph nodes. Biol Cell 1993, 79:27-35 [28]

A.3. Immortalization and Selection of the Cell Lines of Feline Endothelial Cells The cultures of endothelial cells were transfected with the pSV3-neoplasmid (ATCC) described in Bizouarne et al. [28]. The geneticin-resistant cells were cloned and selected by the method described in Bizouarne et al. [27].

The feline endothelial cell lines were cultured in OptiMEM medium (brand name) marketed by the company Invitrogen containing Gibco Glutamax (brand name), 2% of fetal bovine serum, 5% of fungizone (brand name) and 0.4% of gentamicin (brand name). The lines were kept in a humid atmosphere containing 5% of carbon dioxide ($CO_2$) at 37° C.

A.4. Characterization of the Cell Lines of Feline Endothelial Cells

A.4.1. Weibel-Palade Intracellular Bodies ("Weibel-Palade Bodies", WPB) and Detection of Angiotensin Converting Enzyme All the established cell lines were cultured for 48 hours on twelve-well microscope slides marketed by the company (ICN Bio-medicals, 12 Aurora, Ohio, USA). The monolayers were fixed for 10 minutes with paraformaldehyde (PFA) marketed by the company Merck (Darmstadt (Germany)) at a concentration of 10 mg/ml and permeabilized for 30 min at 37° C., with Triton14 X100 at 0.05%.

For detecting the Weibel-Palade intracellular bodies, an anti-human von Willebrand factor rabbit polyclonal antibody marketed under catalog number A0082 by the company Dako at a concentration of 20 µg/ml was applied on the cells for 2 hours at room temperature, i.e. 20° C. and washed twice with phosphate-buffered saline (PBS) containing 1% of bovine serum albumin. The secondary antibody was a rabbit anti-immunoglobulin fluorescent antibody, made in a goat and labeled with fluorescein isothiocyanate at a concentration of 20 µg/ml marketed by the company SBE, CliniSciences, Montrouge, France, with which the cells were incubated for 30 minutes at room temperature.

For detecting the angiotensin converting enzyme of anti-human angiotensin converting enzyme rabbit polyclonal antibodies marketed under reference sc-20791 by the company Santa Cruz Biotechnology, diluted to 1:50 in phosphate-buffered saline (PBS) containing 1% of bovine serum albumin, and a second fluorescent anti-rabbit immunoglobulin goat antibody labeled with fluorescein isothiocyanate was used. The inventors used monkey liver epithelial cells Vero line (ATCC, CCL-81) as negative control. The cells were examined with a Leica DMI 4000 B fluorescence microscope.

A.5.2. Angiogenesis Test

A 96-well plate from the company Falcon, BD Biosciences, Grenoble, France was coated with Matrigel (brand name) marketed by BD Biosciences, Grenoble France to simulate the extracellular matrix at a rate of 40 µl per well. The Matrigel (brand name) was left to polymerize for 1 hour at 37° C. before seeding the cells at a rate of $8 \times 10^3$ cells per well. The rearrangement and formation of capillary-type structures were observed and photographed regularly at different times under a microscope (marketed by Nikon TMS, Japan). The monkey epithelial cells Vero line, ATCC, CCL-81 serve as negative control.

B. Results

Based on their tissue origin, nine endothelial cell lines were established, eight cells from the microvascularization designated as feline skin microvascular endothelial cells (FSkMEC), feline peripheral lymph node microvascular endothelial cells (FPLNMEC), feline lung microvascular endothelial cells (FLuMEC), feline brain microvascular endothelial cells (FBrMEC), feline liver microvascular endothelial cells (FLiMEC), feline Peyer's patches microvascular endothelial cells (FPPMEC), feline intestine microvascular endothelial cells (FIntMEC), feline heart microvascular endothelial cells (FHeMEC) and one line from the macrovascularization designated feline umbilical cord endothelial cells (FUmEC).

The presence of endothelial markers: von Willebrand factor, vWf and angiotensin converting enzyme (ACE) was confirmed by fluorescence microscopy. The cells, permeabilized and treated with an anti-vWf antibody, revealed the presence of Weibel-Palade intracytoplasmic granules. The granules were localized around the nucleus and dispersed in the cytoplasm. Moreover, each feline cell line tested was positive for angiotensin converting enzyme. Its localization was intracellular and on the cell surface (data not supplied).

As one of the functional characteristics of the endothelial cells is supporting angiogenesis, the cell lines were tested for their capacity for producing capillary-type structures in a conventional Matrigel test (brand name). As efficiently as human endothelial cells, the nine established cell lines were capable of producing angiogenesis on Matrigel. FIG. 1 corresponds to photographs illustrating this property.

From the nine established endothelial cell lines, the feline endothelial cells of the skin (FSkMEC) derived from the microvascularization and the feline umbilical cord endothelial cells (FUcEC) derived from the macrovascularization were selected for the next experiments.

This example clearly demonstrates the isolation, characterization and establishment of established lines of feline endothelial cells.

Example 2

Comparative Study Between Human Endothelial Cells and Feline Endothelial Cells

A. Materials and Method

A.1. Cell Lines of Human Endothelial Cells

Two cell lines of organ-specific endothelial cells described in Kieda C, Paprocka M, Krawczenko A, Zalecki P, Dupuis P, Monsigny l M, Radzikowski C Dus D: New human microvascular endothelial cell lines with specific adhesion molecules phenotypes. Endothelium 2002, 9:247-261 [29] were used. One isolated from the macrovascularization: human umbilical vein endothelial cells (HUVEC) and one isolated from the microvascularization of the skin: human skin microvascular endothelial cells (HSkMEC).

A.2. Cell Lines of Feline Endothelial Cells

The cell lines of feline skin endothelial cells (FSkMEC) derived from the microvascularization and the feline umbilical cord endothelial cells (FUmEC) derived from the macrovascularization from example 1 were used.

A.3. Bacterial Strains

Four strains of *B. henselae* were used based on the species of origin: human or feline, and the genotype: I or II. The two strains isolated from human patients were the strains Houston-1 ("strain Houston-1" (genotype I (H1)/ATCC 49882)) and the strain genotype II Marseille (H2) supplied by Jean Marc Rolain (*Rickettsia* Unit, Marseille France). The two strains isolated from cats were a strain of genotype I (F1/ Strain 297172) supplied by Bruno Chomel (University of California, Davis, USA) and a *B. henselae* strain genotype II isolated initially by the inventors by the method described in Gurfield A N, Boulouis H J, Chomel B B, Kasten R W, Heller R, Bouillin C, Gandoin C, Thibault D, Chang C C, Barrat F, Piemont Y. Epidemiology of *Bartonella* infection in domestic cats in France. Vet Microbiol. 2001 May 21; 80(2):185-98 [30].

*B. tribocorum* (Bt) isolated from rats and with no known pathogenicity for humans and cats was used as control.

All the strains were cultured on an agar medium with addition of 5% of sheep blood marketed by the company BioMerieux, Craponne, France, for 5 to 7 days in a humidified atmosphere at 37° C. and 5% $CO_2$.

A.4 Analysis of the Expression of BadA in the *Bartonella* Strains

The inventors verified the presence of pili in the strains used by detecting the antigen of BadA using an immunological method. After 6 days of bacterial growth on an agar medium with sheep blood marketed by the company BioMerieux, Craponne-France, the *Bartonella* strains were recovered and resuspended in PBS. The bacteria were used at a concentration of $2 \times 10^8$ per ml, which was determined by measuring the optical density at 600 nm, with a density equal to 2 indicating a concentration of $10^9$ bacteria per ml according to the protocol described in Riess T, Raddatz G, Linke D, Schäfer A, Kempf V A J: Analysis of *Bartonella* adhesin A expression reveals differences between various *B. henselae* strains. Infect Immun 2007, 75:35-43 [16].

One milliliter of each of the suspensions was introduced into a plastic tube and incubated at 37° C. with 5% $CO_2$ in a humid atmosphere. After 60 minutes, 10 µL of the suspension was taken from the bottom of each tube and transferred onto a glass slide and fixed with 4% of PBS-PFA. After washing with PBS, the nonspecific sites were blocked with 0.2% of BSA for 20 minutes. The bacteria were stained with an anti-Bad A serum rabbit polyclonal antibody supplied by V. Kempf, Klinikum des Johann Wolfgang Goethe Universität, Frankfurt am Main Germany, for 1 hour. A secondary antibody, anti-rabbit immunoglobulin goat antibody labeled with fluorescein isothiocyanate marketed by the company SBE CliniSciences, Montrouge, France, was added. The bacteria were washed with PBS and detection was carried out with a Leica DMI 4000 B fluorescence microscope.

The deoxyribonucleic acid (DNA) was stained with 4'-6 diamidino-2-phenylindole dihydrochloride (DAPI) marketed under catalog reference ref H-1200 by the company AbCys, France as internal control.

A.5 Generation of Culture Supernatants of *Bartonella*

The strains of *B. henselae* and *B. tribocorum* were recovered from plates of agar containing blood and were suspended in Schneider medium marketed by the company Gibco, France. The bacterial cultures were stirred for 18 hours at 200 revolutions per minute (rpm) and at 37° C. on an orbital stirrer. After 18 hours of incubation, the suspensions were taken from the bottles and centrifuged at 2000 rpm for 10 minutes to form a pellet. The supernatants without bacteria were concentrated and diafiltered with OptiMEM using an Amicon Ultra-15 MILLIPORE centrifugal filter (registered trademark). The culture supernatant was obtained by the same method. The protein concentrations were determined by bis inchonitic acid assay with the BC Assay kit (brand name) marketed by the company Uptima, Interchim.

A.6. Induction of Angiogenesis in Vitro

Twenty hours before infection of the endothelial cells HUVEC, HSkMEC, FUmEC and FSkMEC, the antibiotics were removed from the culture medium. The endothelial cells, $8 \times 10^3$ cells per well, were infected with *Bartonella* at a multiplicity of infection (MOI) of 50, 100 and 150 bacteria per cell or treated with culture supernatant at 250 µg/ml. They were then seeded in 96-well plates coated beforehand with 40 µl per well of Matrigel (brand name) (BD Biosciences, Grenoble, France). The rearrangement of the endothelial cells and the formation of capillary-type structures were acquired and recorded for image analysis by the Zeiss axiovision program. The Zeiss axiovert 200M video microscope equipped for control of temperature, gas and humidity was used for acquiring images at time intervals and for reconstituting the kinetics of the dynamic process of angiogenesis. The formation of pseudo-vessels was monitored for 7 days. The formation of capillary-type structures was quantified by measuring the length of the tubes and the number of branch points.

A.7. Cicatrization Test

The HUVEC, HSkMEC, FUmEC and FSkMEC cells were seeded in a 24-well plate at a density of $10^5$ cells per well and left in OptiMEM medium without antibiotics overnight. When the cells reached confluence, a rectilinear wound was made at the center of the well using the end of a sterile pipette cone. The endothelial cells were infected with bacteria at a MOI of 100 for 24 hours. Cicatrization was observed and photographed under a Nikon TMS microscope (brand name). The cicatrization distances (in 21 µm) were measured at time 0 and at 24 hours after making the wound.

A.8 Determination of the Intracellular Level of cAMP

After infection of the HUVEC, HSkMEC, FUmEC and FSkMEC endothelial cells with the *Bartonella* strains at a MOI of 150 for 30 hours in a 24-well plate, the cells were washed with PBS and lysed. The intracellular levels of cAMP were determined by the EIA system (brand name) marketed by the company Biotrak, Amersham, Biosciences according to the manufacturer's recommendations.

A.9. Analysis of VEGFR-2 by Western Blot Analysis

After 24 hours of infection of HUVEC, HSkMEC, FUmEC and FSkMEC endothelial cells with various bacteria at a MOI of 100, the HUVEC, HSkMEC, FUmEC and FSkMEC cells were lysed in TNT lysis buffer comprising 10 mM of Tris-HCl pH 7.5; 150 mM NaCl; 1% Nonidet P-40; 1% Triton X100 and 2 mM of EDTA supplemented with inhibitors of proteases and phosphatases namely 10 µg/ml of leupeptin and aprotinin, 1 mM of phenylmethylsulfonyl fluoride; 25 mM of NaF and 300 µM of vanadate, for 15 minutes at 4° C. Equal quantities of samples were submitted to electrophoresis on polyacrylamide gel containing SDS and were transferred to a polyvinylidene difluoride membrane.

The membranes were incubated with an anti-VEGF-R2 antibody and anti phosphorylated VEGFR-2Y1175 marketed by the company Cell signaling, Ozyme, Saint-Quentin-en-Yvelines, France. The antibodies were then detected using the fluorescent dye dylight680 fluorescent marketed by the company Pierce Biotechnology conjugated with secondary antibodies and the membranes were scanned and analyzed with the infrared imaging system Odyssey (brand name) marketed by the company Li-Cor BioSciences, EuroSep, Cergy-Pontoise, France.

B. Results

Figure 2:
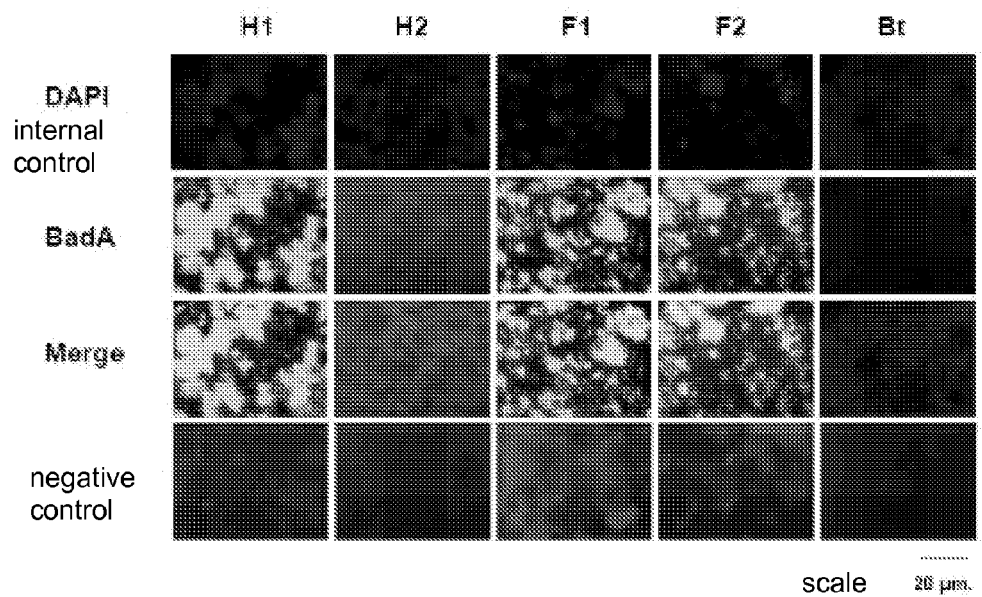
FIG. 2 shows photographs of the expression of different strains of *B. henselae* and of *B. tribocorum*. Various markers were used diamino-2-phenylindole chloride (DAPI): line DAPI, an anti BadA antibody labeled with a green fluorochrome: line BadA, and the two stains mixed together: merge line, and a negative control for which no marker is used. Photographs were also taken representing a negative control. The various strains were the strains H1: human *B henselae* strain, genotype I, H2: human B henselae strain genotype II, F1: *B henselae* strain, American feline type I, F2: *B henselae* strain, American feline type II and Bt: *B. tribocorum* used as control.

B.1. Determination of Expression of BadA in the *B. henselae* and *B. tribocorum* Strains BadA has been characterized as being an important pathogenic factor for *B. henselae* and must be evaluated before experiments of infection with *B. henselae*. Three *B. henselae* strains (H1, F1 and F2) express BadA, whereas *B. henselae* (H2) and *B. tribocorum* do not express it. FIG. 2, showing the expression of Bad-A, clearly demonstrates these results: line BadA column H1, F1 and F2. Moreover, only the strains positive for BadA, H1, F1 and F2, are self-agglutinating, whereas the strains not expressing BadA: H2 and Bt, were not self-agglutinating, as FIG. 2 shows.

B.2. Angiogenic Response of Feline and Human Endothelial Cells to *Bartonella*

The capacity of the uninfected human and feline cell lines for forming capillary-type structures was evaluated first by culture on Matrigel (brand name). The inventors demonstrated that capillary-type structures of uninfected feline endothelial cells appeared rapidly in the two hours after seeding, whereas with uninfected human endothelial cells derived from the macrovascularization (HUVEC), these structures appear in about 5 hours and in about 10 hours with the endothelial cells derived from the microvascularization (HSkMEC).

Unlike the feline endothelial cells, the network of pseudo-vessels persists for a longer time with human endothelial cells. In fact, the network persists for up to 24 hours for human endothelial cells derived from the macrovascularization and for up to 7 days for human endothelial cells from the microvascularization, whereas for feline endothelial cells this network disappears after 20 hours.

These results therefore clearly demonstrate that the cellular characteristics of the feline endothelial cells are different from those of the human endothelial cells.

B.3. Study of *Bartonella* Infection of Cell Lines of Feline Endothelial Cells and of Cell Lines of Human Endothelial Cells The inventors also observed the effects of *Bartonella* infection on four cell lines, namely feline skin endothelial cells (FSkMEC) derived from the microvascularization and feline umbilical cord endothelial cells (FUmEC) derived from the macrovascularization, human endothelial cells derived from the macrovascularization (HUVEC) and human endothelial cells derived from the microvascularization (HSkMEC).

For the HSkMEC cells, regardless of the origin of the species and of the genotypes of *Bartonella* used, formation of the network of the capillary type was dose-dependent. For higher MOI, formation of capillary tubes is quicker, relative to uninfected HSkMEC cells. Infections with lower MOI, of 50 and 100, also accelerated the formation of capillary tubes relative to uninfected cells, as shown in FIG. 3A HSkMEC-H1 MOI 50, and HSkMEC-H1 MOI 100.

Figure 3:
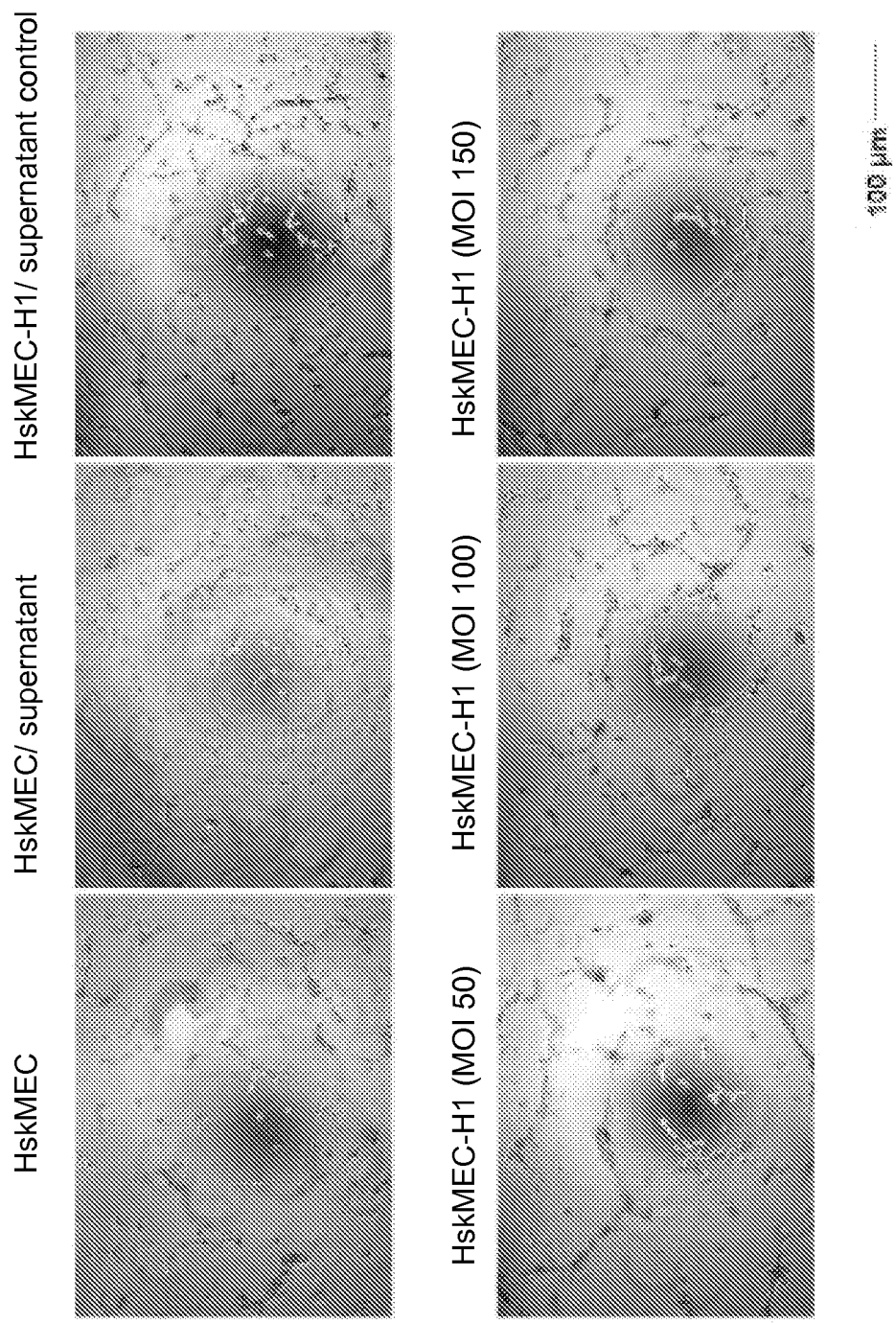
FIG. 3A shows photographs of culture of endothelial cells of the invention and the effect of infection with the human type I *B henselae* strain on the formation of capillary structures. This figure shows the effect as a function of the multiplicity of infection (MOI) equal to 50, 100 or 150 MOI.
FIG. 3B shows histograms representing the length of the tubes in micrometers as a function of the human microvascular endothelial cells of human skin (HSkMEC: "human skin microvascular endothelial cells") and of their treatment with the various bacterial strains or their culture supernatant. Thus: skin (HSkMEC: "human skin microvascular endothelial cells") "human skin microvascular endothelial cells"), namely HSkMEC: uninfected cell, HSkMEC H1: cell infected with *B. henselae* Houston-1 ("strain Houston-1" (genotype I (H1)/ATCC 49882)), HSkMEC SH1 cell treated with the culture supernatant from H1, HSkMEC F1 cell infected with a *B. henselae* strain isolated from cats of genotype I (F1/Strain 297172), HSkMEC SF1 cell treated with the culture supernatant from F1, HSkMEC F2 cell infected with a *B. henselae* strain isolated from cats of genotype II, HSkMEC SF2 cell treated with the culture supernatant of F2, HSkMEC tribo cell infected with *B. tribocorum* (Bt), HSkMEC S tribo cell treated with the culture supernatant of Bt; and the number of branchings as a function of these same cells (FIG. 3b).
Figure 3:
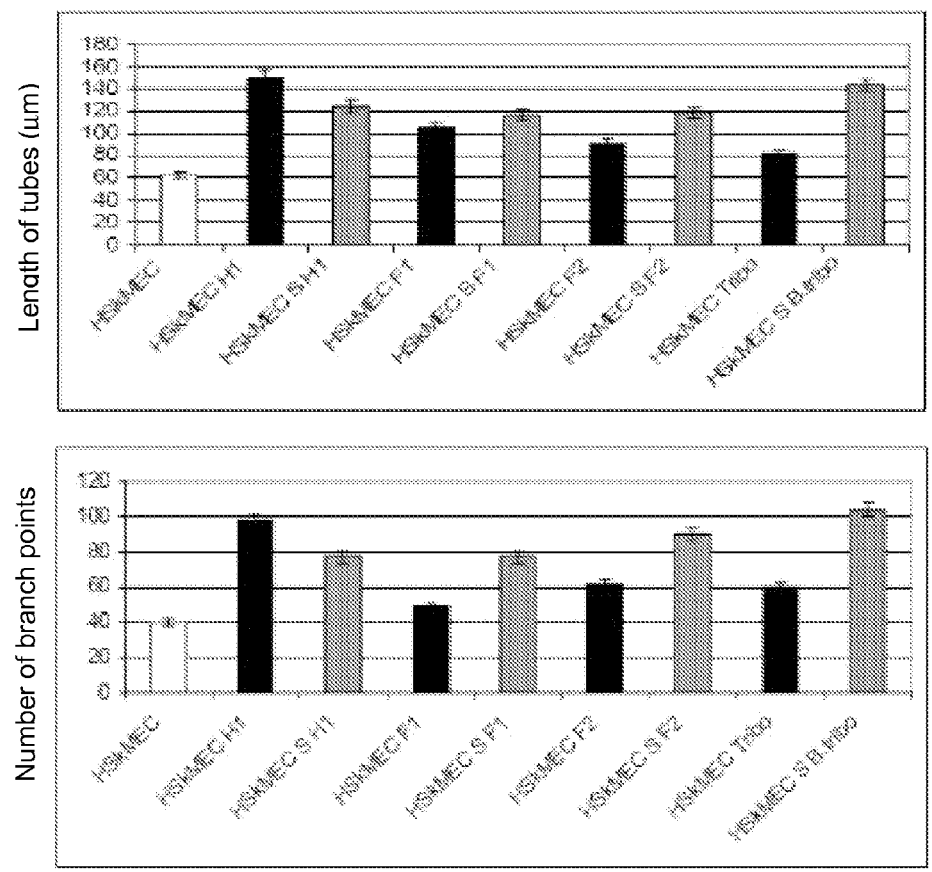

Moreover, the HSkMEC cells infected with *Bartonella* have an elongated morphology compared to the cells of the control, as shown in FIG. 3A. Finally, for HSkMEC cells infected with *Bartonella*, the density of capillary-type structures is roughly doubled compared to uninfected cells. This increase can be seen clearly in FIG. 3B. The network was observed for up to 7 days with these cells and then it disappeared.

For the HUVEC cells, the density of the capillary-type structures is roughly doubled in the infected cells compared to the uninfected cells. However, this formation was not earlier. Moreover, this network was only observed for up to 24 hours before disappearing.

No visible difference was observed in the kinetics of formation of capillary-type structures when the FUmEC and FSkMEC cells were cultured on Matrigel (brand name), regardless of the origin of the host and the genotype of *Bartonella* used.

However, 2 hours after seeding, angiogenesis of FUmEC and FSkMEC had already begun. Moreover, destruction of the network is more rapid in the infected cell lines compared to the uninfected cell lines (results not supplied). Thus, the effect of *Bartonella* on network formation was greater on human endothelial cells than on feline endothelial cells and was dose-dependent. Moreover, the effect was more persistent on human endothelial cells from the microvascularization relative to the macrovascularization.

These results clearly demonstrate that the feline and human endothelial cells do not react in the same way to infection by a pathogenic microorganism.

These results also clearly demonstrate that the cells of the invention can be used as a cellular model for monitoring and/or demonstrating species specificity of infectious diseases.

These results also clearly demonstrate that the cells of the invention can be used for demonstrating and studying the specificity and targeting of one endothelial type relative to another in terms of vascular characteristics.

B.4. Angiogenic Response of Endothelial Cells to the Culture Supernatants of *Bartonella*

In order to study the effects of the secretome of *Bartonella*, various culture supernatants of *Bartonella* were generated and tested for their capacity for inducing angiogenesis of feline and human endothelial cells. At a protein concentration of 250 µg/mL, the culture supernatants of *Bartonella Bartonella* induced formation of capillary tubes in human endothelial cells as shown in FIG. 3A).

The angiogenic responses obtained with the culture supernatants of *Bartonella* were accelerated two-fold in comparison with the control cells, such as during infection of the cells with *Bartonella* at a MOI of 150 (FIGS. 3A and 3B).

The morphology of human endothelial cells incubated with the culture supernatant was similar to that of the cells infected with *B. henselae* at MOIs of 50, 100 or 150 as shown in FIG. 3A.

Moreover, the culture supernatant did not speed up the angiogenesis of feline endothelial cells.

These results clearly demonstrate that the cells of the invention can be used notably for screening molecules, thus making it possible to determine whether these molecules have an effect on the cells, for example whether they have an effect on angiogenesis.

These results also clearly demonstrate that we can elucidate the mechanisms of the activity of a pathogen using the cells of the invention, that the cells of the invention can be used for demonstrating the species specificity of the activity of a pathogen and/or that the molecular mechanism of the action of the microorganism can be determined by means of the cells of the invention.

B.5. Investigation of the Effect of Infection with *Bartonella* on the Migration/Cicatrization of Endothelial Cells Induced by a Wound The migration of endothelial cells is an essential step for angiogenesis. This experiment examined the importance of the site of infection with respect to the susceptibility of the endothelium.

Figure 4:
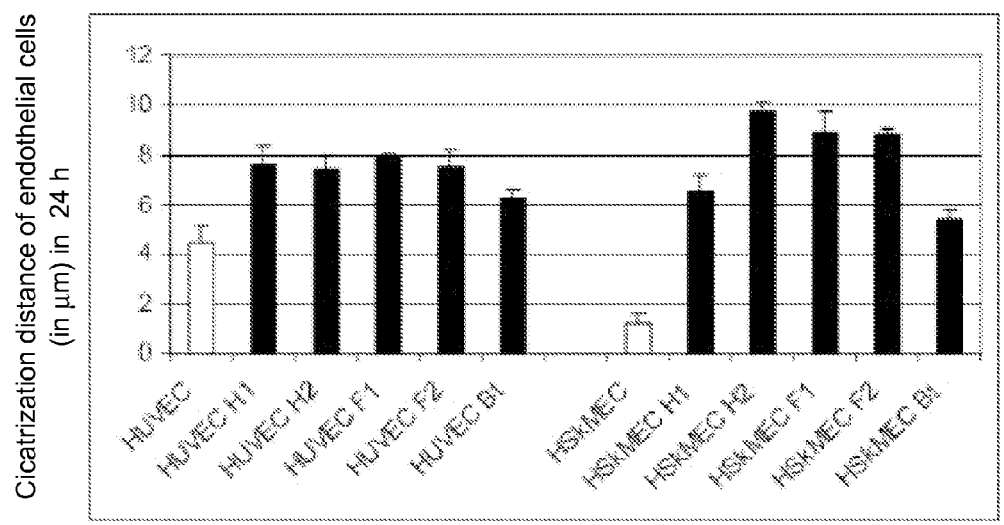
FIG. 4 gives a histogram showing the length of cicatrization in micrometers in 24 hours, of human endothelial cells isolated from the macrovascularization of the vein of the umbilical cord (HUVEC: "human umbilical vein endothelial cell") and one isolated from the microvascularization, human skin microvascular endothelial cells (HSkMEC) infected with various bacterial strains, namely HSkMEC H1: HSkMEC cell infected with *B. henselae* Houston-1 ("strain Houston-1" (genotype I (H1)/ATCC 49882)), HSkMEC F1: HSkMEC cell infected with a *B. henselae* strain isolated from cats of genotype I (F1/Strain 297172), HSkMEC F2: HSkMEC cell infected with a *B. henselae* strain isolated from a cat, of genotype II, HSkMEC Bt: HSkMEC cell infected with *B. tribocorum* (Bt), HUVEC H1: HUVEC cell infected with *B. henselae* Houston-1 ("strain Houston-1" (genotype I (H1)/ATCC 49882)), HUVEC F1: HUVEC cell infected with a *B. henselae* strain isolated from a cat, of genotype I (F1/Strain 297172), HUVEC F2: HUVEC cell infected with a *B. henselae* strain isolated from a cat, of genotype II, HUVEC Bt: HSkMEC cell infected with *B. tribocorum* (Bt).

The reaction of the endothelial cells depending on their tissue origin was observed after infection by measuring their speed of migration for cicatrization of a mechanical wound. Uninfected, the HUVEC cells cicatrize the wound at least 5 times quicker than the HSkMEC cells but infection induces an acceleration of cicatrization of the HUVEC and HSkMEC cells. Moreover, the speed of healing of HUVEC cells was approximately doubled whereas it increases by a factor 4 to 7 for the HSkMEC cells (FIG. 4).

Wound-induced migration was also observed for the FUmEC and FSkMEC feline endothelial cells but no stimulation by infection with *Bartonella*.

These results clearly demonstrate that the cells of the invention are useful for verifying the biological validity of the observation of species specificity and for determining the effect of molecules that can act on infectious agents and/or microorganisms.

B.6. Effect of Infection with *Bartonella* on Human and Feline Endothelial Cells on the Production of cAMP The level of cAMP induced by infection of four endothelial cell lines with various *Bartonella* showed that infection of HUVEC endothelial cells with the strain of genotype I of *B. henselae* triggered production of cAMP.

In feline endothelial cells from the macrovascularization and microvascularization, the cAMP level produced by feline FUcEC and FSkMEC cells was lower than the cAMP level produced by human HUVEC and HSkMEC endothelial cells.

Figure 5:
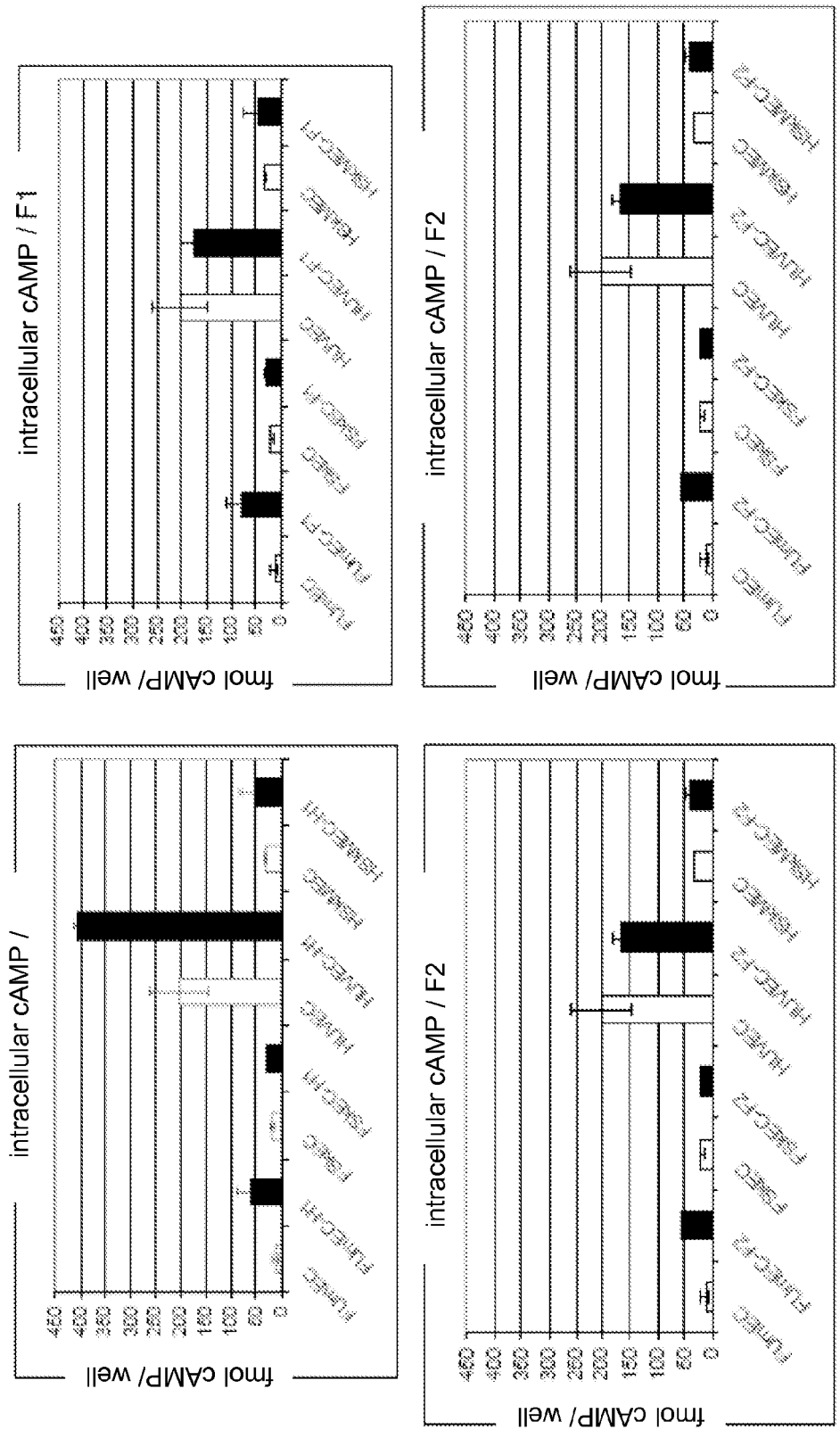
FIG. 5 shows histograms of the intracellular production of cAMP in human umbilical vein endothelial cells (HUVEC), human endothelial cells from human skin (HSkMEC: "human skin endothelial cells"), feline skin endothelial cells (FSkMEC) and feline umbilical cord endothelial cells (FUcEC) in relation to infection thereof with a *B. henselae* strain isolated from cats of genotype I (F1), *B. henselae* of genotype I (H-1) ("strain Houston-1" genotype I (H1)/ATCC 49882), a *B. henselae* strain of genotype II isolated from cats (FII) and *B. tribocorum* (Bt).

The level produced by the macrovascular HUVEC cell was higher relative to the production of cells from the microvascularization (HSkMEC). For feline endothelial cells, no difference was observed between the endothelial cells from the macrovascularization and from the microvascularization with respect to very low production of cAMP. These results are clearly described in FIG. 5.

In the infected endothelial cells, the amounts of cAMP produced by human and feline cells from the macrovascularization were greater than those produced by cells from the microvascularization.

The HUVEC cells infected with strain H1 (human) produced a higher level of cAMP. However, infection of HUVEC cells with other strains such as the feline strains F1, F2 and the Bt strain did not induce such production of cAMP.

Infection of human and feline endothelial cells from the microvascularization induced a slight increase in cAMP, indicating that the process of activation of cAMP signalling by bacterial infection is species-dependent and organ-dependent.

These results clearly demonstrate that the cells of the invention therefore make it possible to study and elucidate the mechanisms of infection as a function of organ, vascular type and species.

B.7. Effects of Infection with *B. henselae* on Activation of VEGFR-2

The vascular endothelial growth factor (VEGF) is the main angiogenic factor regulating, in a positive manner, the migration, proliferation and survival of endothelial cells. Induction of the production of VEGF by macrophages by infection with *Bartonella* was suggested in the prior art in vivo and in vitro.

This example examines the level of activation of the VEGF receptor, VEGFR-2, which is implicated in the proangiogenic effects.

Figure 6:
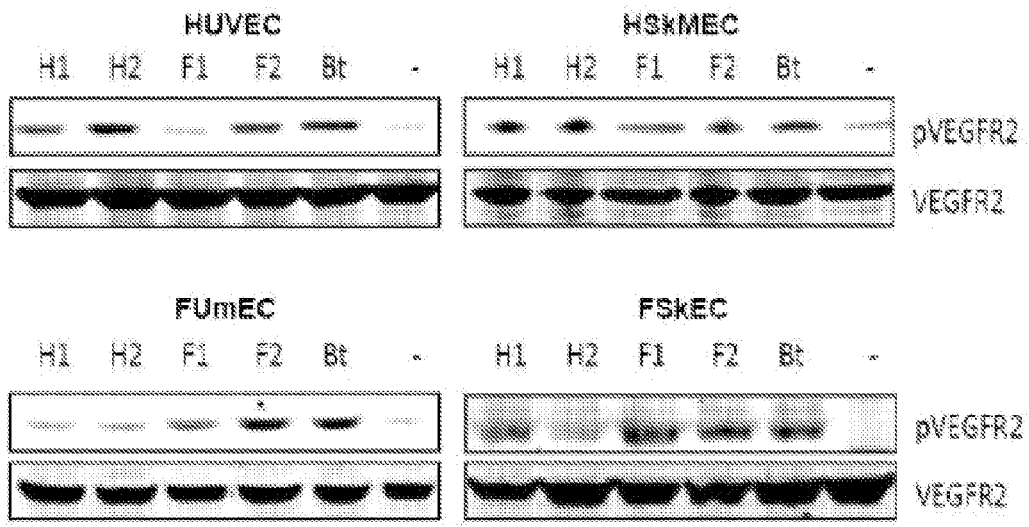
FIG. 6 shows photographs of Western Blots corresponding to expression of VEGF receptor 2 (VEGFR-2) and of phosphorylated VEGF receptor 2 (pVEGFR-2) in FSkMEC, FUcEC, HSkMEC, HUVEC cells infected with a *B. henselae* strain of genotype I (F1) isolated from cats, *B. henselae* of genotype I (H-1) ("strain Houston-1" genotype I (H1)/ATCC 49882), *B. henselae* of genotype II (H2), a *B. henselae* strain of genotype II isolated from cats (FII) and *B. tribocorum* (Bt).

The inventors have shown that *Bartonella* infection of HUVEC, HSkMEC, FUmEC and FSkEC endothelial cells is associated with an increase in phosphorylation of VEGFR-2 (FIG. 6).

Moreover, the inventors have shown that the level of phosphorylated VEGFR-2 is higher when the cells are infected with a strain derived from a homologous host, i.e. when human endothelial cells are infected with strains originally infecting humans and isolated from humans and when feline endothelial cells are infected with strains originally infecting cats and isolated from cats.

This example clearly demonstrates that there is a mechanism linking the species of endothelial cells with the bacterial infection and that the invention can be used for demonstrating this species specificity of a pathogen.

C. Discussion

*B. henselae* is a facultative intracellular pathogen associated with the induction of vasoproliferative tumors in humans but not in cats.

Angiogenic stimulation by infection with *B. henselae* is a characteristic of bacterial pathogenicity and is of particular interest for understanding the formation of tumors caused by bacteria. However, only a small amount of contradictory data has been obtained concerning the mechanisms involved in angiomatous diseases induced by *B. henselae*. Conley et al. [18] showed that the stimulating factor of *B. henselae* is a protein localized in a particulate fraction whereas others have supplied evidence of soluble factors secreted by the bacteria.

The examples clearly demonstrate the need to use organ-specific endothelial cells for studying the interactions between *B. henselae* and endothelial cells. Moreover, it is important to compare the results obtained with human cells with those supplied by feline endothelial cells. This example clearly demonstrates a difference in reactivity between human cells and feline cells and between the cells of the macrovascularization and of the microvascularization.

This example also clearly demonstrates the need to have established cell lines of feline endothelial cells as well as established cell lines of organ-specific cells of the microvascularization and of the macrovascularization.

The cells of the invention therefore make it possible to study and elucidate the mechanisms of infections as a function of the organ, vascular type and species.

Moreover, when there is infection, it is necessary to consider the local physiological conditions: the microenvironment. To do this, and as this example clearly demonstrates, the cells of the invention constitute a novel tool that is very useful notably for studying the cellular and bacterial factors determining the reactivity of pathogenic microorganisms in humans relative to cats, how it produces, for example, anti-apoptotic and/or proangiogenic mechanisms resulting from bacillary angiomatosis and from peliosis only in humans.

Moreover, the results obtained show that the effects on cells derived from the microvascularization cannot be represented completely by cells derived from the macrovascularization.

Moreover, the results obtained were able to demonstrate the intrinsic differences in angiogenic kinetics and in cicatrization between human endothelial cells derived from the microvasculature and macrovascularization.

The endothelial response to infection with *Bartonella* appears to act at two levels of the angiogenic process. Acceleration of rearrangement of the cells was only observed with human endothelial cells derived from the microvascularization whereas the quantity of pseudo-vessels was increased with microvascular and macrovascular human endothelial cells.

The results show that macrovascular and microvascular feline endothelial cells are different. In fact, infection with *B. henselae* does not have a visible proangiogenic effect in-vitro but accelerates destruction of the network of feline cells. These results recapitulate the clinical situation, i.e. absence of pseudotumoral lesions in cats whereas in humans BA.

The cells of the invention therefore constitute a novel tool that is very useful notably for understanding the molecular and cellular basis of the zoonotic potential of *B. henselae* and for exploring the molecular and cellular mechanisms underlying BA/BP.

Moreover, the above examples demonstrate that although *B. henselae* causes proliferation of HUVEC cells in vitro, proliferation is inhibited at higher MOIs owing to the cytotoxic effect of the type four secretion system encoded by virB.45. However, endothelial proliferation is only one part of angiogenesis, which also comprises migration of endothelial cells, survival of the cells in new types of extracellular matrixes, differentiation and organization as networks of vessels. For the HSkMEC cells, the increase in formation of capillary-type structures and early manifestation of capillary formation was increased with high MOIs.

No cytotoxic effect of VirB was exerted during the experiments of formation of angiogenesis, even at the highest dose used, as was suggested in the prior art for HUVEC cells.

The model of infection based on human endothelial cells of the microvascularization also tends to show that, independently of the bacterial species *B. henselae* or *B. tribocorum*, or of the genotype (I or II) of *B. henselae*, all the strains of *Bartonella* tested can induce the same angiogenic effects in vitro.

The results showed that for acceleration of the angiogenic process in vitro, direct contact of the bacterium with the endothelial cells was not necessary. Thus, the bacterium *B. henselae* must produce and secrete endothelial growth factors.

Previous studies of the interactions between HUVEC cells and *B. henselae* of genotype I demonstrated the production of cAMP in the activity of *B. henselae*.

Unlike HUVEC cells, the HSkMEC cells do not produce a high level of cAMP. These results therefore confirm the results obtained previously with HUVEC cells. In fact, it is necessary to take account of HUVEC cells, which are cells derived from the macrovascularization, and therefore are very different from the endothelial cells from the microvascularization. The HSkMEC cells represent a model of microvascular endothelial cell of the skin, implicated clinically in angiomatosis and bacillary peliosis.

As shown by the results obtained, the cAMP levels produced by feline microvascular or macrovascular endothelial cells were always significantly lower than those produced by human cells independently of infection, indicating a difference in reactivity between the two species.

Finally, the results also demonstrate the activation, which is reflected in phosphorylation of VEGF receptor 2 (VEGFR-2). However, the latter is not phosphorylated during infection by homologous strains. It is known that VEGF is the key factor in angiogenesis. Thus, increase in phosphorylation of VEGFR-2 and therefore its activation during infection by homologous strains may reflect the existence of adaptive control of *B. henselae* to the different host species and therefore contribute to its susceptibility in humans. Activation of VEGFR-2 by *Bartonella* shows that VEGF has bound to its receptor and that the activation signal is normally expressed by phosphorylation of the molecule. Moreover, it was shown in the prior art that patients with BA or BP; or with a verruca peruviana induced by *Bartonella bacilliformis* had a high level of VEGF or strong expression of VEGF receptors 1 and 2 by the endothelial cells. It is therefore highly probable that VEGF is one of the factors involved.

As demonstrated by the results, the cells of the invention therefore also make it possible to identify molecules involved in cellular mechanisms.

This example therefore clearly demonstrates, by the results obtained for angiogenesis in vitro, stimulation of wound healing, induction of cAMP and activation of VEGFR-2, the importance of the tissue origin of the endothelial cells and the specificity of the relation between the various strains of *B. henselae* and of the human cell lines versus feline cell lines.

Example 3

Screening of Molecules for Identifying Molecules Capable of Inducing, or of Inhibiting Angiogenesis of Feline Endothelial Cells The cells used in this example are those isolated and characterized in example 1 above.

The culture medium used is OptiMEM medium (brand name) marketed by the company Invitrogen containing Gibco Glutamax (brand name), 2% of fetal calf serum, 5% of fungizone (brand name) and 0.4% of gentamicin (brand name).

The various cells are cultured independently in different wells for 24 hours in a humid atmosphere containing 5% of carbon dioxide ($CO_2$) at 37° C.

Then the molecule to be tested is introduced into the culture medium. A control without the molecule is carried out in the same conditions and corresponds to the negative control. The cells are cultured for 24 hours at 37° C.

The effect of the molecule on the angiogenesis of endothelial cells is observed with the microscope at different times according to the protocol described in example 2.

The molecule tested stimulates angiogenesis if the appearance of capillary-type structures is accelerated relative to the negative control. Conversely, if the appearance of capillary-type structures is delayed, or nonexistent relative to the negative control, the molecule inhibits angiogenesis.

Example 4

Screening of Molecules for Identifying Molecules that may have an Action on a Pathogenic Microorganism The cells used in this example are those isolated and characterized in example 1 above.

The culture medium used is OptiMEM medium (brand name) marketed by the company Invitrogen containing Gibco Glutamax (brand name), 2% of fetal calf serum, 5% of fungizone (brand name) and 0.4% of gentamicin (brand name).

The various cells are cultured independently in different wells for 48 hours in a humid atmosphere containing 5% of carbon dioxide ($CO_2$) at 37° C.

The microorganisms used are the bacteria used in example 2, section A.3, and cultured according to the protocol described in example 2 or the strict intracellular microorganisms stated in example 5.

Twenty-four hours before infection of the endothelial cells, the antibiotics are removed from the culture medium. The endothelial cells, at a rate of $3 \times 10^4$ cells per well, are infected independently with a bacterium at a multiplicity of infection (MOI) of 100 bacteria per cell or treated with bacterial culture supernatant no longer containing bacteria and representing the negative control of infection.

After introduction of the bacteria, the molecule to be tested is introduced into the culture media with the exception of one medium per cell corresponding to the negative control.

The cells are cultured for 24 hours. After removing medium containing antibiotic, the cells are collected and lysed by freezing and thawing and the lysate is cultured in order to determine the bacterial concentration in the cell. For studying the effect of molecules that may have an action on strict intracellular microorganisms, the effect is evaluated by quantification of the intracellular bacteria by immunofluorescence or by quantitative PCR. If the increase in bacterial concentration is identical to that of the negative control, the molecule tested has no effect, and conversely, if the bacterial concentration is decreased or zero, the molecule tested is active on the bacterium and moreover permits inhibition of its growth.

Example 5

Production of Specific Microorganisms of Feline Endothelial Cells

The cells used in this example are those isolated and characterized in example 1 above.

The culture medium used is OptiMEM medium (brand name) marketed by the company Invitrogen containing Gibco Glutamax (brand name), 2% of fetal calf serum, 5% of fungizone (brand name) and 0.4% of gentamicin (brand name).

The various cells are cultured independently in different tubes for 24 hours in a humid atmosphere containing 5% of carbon dioxide ($CO_2$) at 37° C.

The microorganisms used are the obligate intracellular bacteria *Mycoplasma haemofelis* and *Mycoplasma haemominutum*, *Rickettsia* spp., *Anaplasma phagocytophilum* which are specific microorganisms of endothelial cells and are able to reproduce by infecting feline endothelial cells.

Twenty-four hours before infection of the endothelial cells, the antibiotics are removed from the culture medium. The microorganisms are introduced into each well and the cells are cultured for twenty-four hours at 37° C. (*Mycoplasma haemofelis* and *Mycoplasma haemominutum*, *Anaplasma phagocytophilum*) or 30° C. (*Rickettsia felis*).

The microorganisms are then recovered either by lysis of the cells and recovery of the lysate or by recovering whole infected cells.

Example 6

Production of Specific Chemokines of Feline Endothelial Cells

The cells of the present invention make it possible to produce soluble factors characteristic of the feline species, in an organ-specific manner. Production of the chemokine CCL21 from the endothelial cells from the microvascularization of peripheral lymph nodes; chemokine CXCL16 from the endothelial cells from the microvascularization of the skin; chemokine CCL28 (MEC) from the endothelial cells from the microvascularization of the lung.

The cells are cultured in the culture medium described in example 1 above and in hypoxic conditions, i.e. in an environment in which the value of $pO_2$ is between 1 and 2%. This value of pO$_2$ causes specific activation of the endothelial cells, thus inducing production of the chemokines.

Example 7

Investigation of the Effect of Infections of Feline and Human Endothelial Cells by Strains of *Bartonella* on Production of VEGF in the Culture Medium The cells were cultured in the culture medium described in example 1.

The concentration of VEGF in the culture medium was measured using an ELISA kit for human VEGF marketed by the company R & D Systems, Minneapolis, Minn., USA and used according to the supplier's recommendations.

The cells were seeded at a density of 5×10$^4$ cells/0.5 ml/well in a 24-well plate and left to stand for 12 hours. Then the cells were infected with various strains of *Bartonella* at a MOI of 100. After 72 hours of incubation, the culture medium was recovered. The number of cells was determined immediately after recovery of the cells using a Coulter counter.

The various cells used were HSkMEC human endothelial cells, immortalized HUVEC cells (iHUVEC), FSkMEC cells and feline umbilical cord endothelial cells (FUmEC) as described above. One million cells were tested for each type of cell.

The various strains of *Bartonella* used were: the human type I (H1) *B. henselae* strain (reference ATCC 49882), the human type II (H1) *B. henselae* strain, the feline type I (F1) *B. henselae* strain (reference F1 297172), the feline type II (F2) *B. henselae* strain and *B. tribocorum*.

Figure 7:
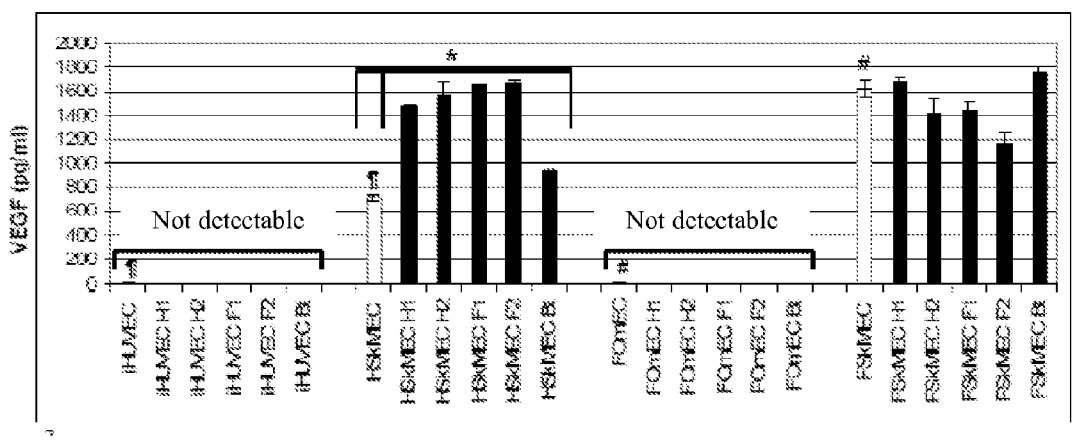
FIG. 7 shows histograms of VEGF production by human endothelial cells HSkMEC, by immortalized HUVEC cells (iHUVEC), by FSkMEC cells and by feline umbilical cord endothelial cells (FUmEC) after infection with various strains of *Bartonella*. The ordinate shows the amount of VEGF measured in picograms per milliliter (pg/ml).

FIG. 7 shows the mean values of measurements of VEGF obtained by ELISA of culture media from the various cells mentioned above infected with one of the various strains mentioned above. The results represent the mean value plus or minus standard deviation.

As shown in FIG. 7, the effect of infection on the production of VEGF by the cells is different from one type of cell to another. The production of VEGF is increased in human cells from the microvasculature: HskMEC after infection.

Thus, the inventors have demonstrated the involvement of VEGF in the action of *B. henselae* in light of the tissue origin. Differential production was demonstrated between uninfected endothelial cells of the microvasculature and of the macrovasculature, whether of human or feline origin.

Moreover, the four different strains of *B. henselae* significantly increase the production of VEGF by the HSkMEC cells (by a factor of 2) whereas the strain *B. tribocorum* increases said production to a smaller extent (by a factor of 1.3).

Moreover, the production of VEGF by the feline cells is not significantly affected by infection with the different strains (FIG. 7).

Finally, the inventors obtained similar results for the production of interleukin 8 (IL8) by the cells as a function of their tissue origin and/or species (results not supplied).

As demonstrated in this example, the cells of the invention therefore make it possible to study the differential expression of significant factors of pathologies. Moreover, the cells of the invention make it possible to study these effects in relation, for example, to the tissue origin of the cells.

Moreover, the cells of the invention can be used, for example, in tests of inflammations and/or tests evaluating the possible effects of compounds, for example anti-inflammatory agents, as a function of the different species and depending on the pathology.

REFERENCES

1. Regnery R L, Anderson B E, Clarridge J E, Rodriguez-Barradas M C, Jones D C, Carr J H: Characterization of a novel *Rochalimaea* species, *R. henselae* sp. nov., isolated from blood of a febrile, human immunodeficiency virus-positive patient. J Clin Microbiol 1992, 30:265-274
2. Boulouis H J, Haddad N, Vayssier-Taussat M, Maillard R, Chomel B: Persistent *Bartonella* infection: epidemiological and clinical implications. Bull Acad Natl Med 2007, 191:1037-10 1044
3. Koehler J E, Sanchez M A, Garrido C S, Whitfeld M J, Chen F M, Berger T G, Rodriguez-Barradas M C, Leboit P E, Tappero J W: Molecular epidemiology of *Bartonella* infections in patients with bacillary angiomatosis-peliosis. N Engl J Med 1997, 337:1876-1883
4. Boulouis H J, Chang C C, Henn J B, Kasten R W, Chomel B B: Factors associated with the rapid emergence of zoonotic *Bartonella* infections. Vet Res 2005, 36:383-410
5. Yamamoto K, Chomel B B, Kasten R W, Hew C M, Weber D K, Lee W I: Experimental infection of specific pathogen free (SPF) cats with two different strains of *Bartonella henselae* type I: a comparative study. Vet Res 2002, 3:669-684
6. Breitschwerdt E B: Feline bartonellosis and cat scratch disease. Vet Immunol Immunopathol 2008, 123:167-71
7. Bergmans A M, Schellekens J, van Embden J, Schouls L M: Predominance 1 of two *Bartonella henselae* variants among cat-scratch disease patients in the Netherlands. J Clin Microbiol 1996, 34:254-260
8. Sander A, Ruess M, Deichmann K: Two different genotypes of *Bartonella henselae* in children with cat-scratch disease and their pet cats. Scand J Infect Dis 1998, 30:387-391
9. Sander A, Posselt M, Bohm N, Ruess M, Altwegg M: Detection of *Bartonella henselae* DNA by two different PCR assays and determination of the genotypes of strains involved in histologically defined cat scratch disease. J Clin Microbiol 1999, 37:993-997
10. Fournier P E, Robson J, Zeaiter Z, Mc Dougall R, Byrne S, Raoult D: Improved culture from lymph nodes of patients with cat scratch disease and genotypic characterization of *Bartonella henselae* isolates in Australia. J Clin Microbiol 2002, 40:3620-3624
11. Dillon B, Valenzuela J, Don R, Blanckenberg D, Wigney D I, Malik R, Morris A J, Robson J M, Iredell J: Limited diversity among human isolates of *Bartonella henselae*. J Clin Microbiol 2002, 40:4691-4699
12. Woestyn S, Olivé N, Bigaignon G, Avesani V, Delmée M: Study of genotypes and virB4 secretion gene of *Bartonella henselae* strains from patients with clinically defined cat scratch disease. J Clin Microbiol 2004, 42:1420-1427
13. Bouchouicha R, Durand B, Monteil M, Chomel B, Berrich M, Birtles R, Breitschwerdt E, Koehler J, Kasten R, Petit E, Maruyama S, Arvand M, Boulouis H-J, Haddad N: Epidemiological applications of Multi-locus Variable number tandem 1 repeat Analysis (MLVA) for *Bartonella henselae* of Human and Feline origins. Emerg Infect Dis 2009, 15: 813-816
14. LeBoit P E, Berger T G, Egbert B M, Beckstead J H, Yen T S B, Stoler M H: Bacillary angiomatosis: The histopathology and differential diagnosis of a pseudoneoplastic infection in patients with human immunodeficiency virus disease. Am J Surg Pathol 1989, 13:909-920
15. Batterman H J, Peek J A, Loutit J S, Falkow S, Tompkins L S: *Bartonella henselae* and *Bartonella quintana* adherence to and entry into cultured human epithelial cells. Infect Immun 1995, 63:4553-4556
16. Riess T, Raddatz G, Linke D, Schäfer A, Kempf V A J: Analysis of *Bartonella* adhesin A expression reveals differences between various *B. henselae* strains. Infect Immun 2007, 75:35-43
17. Riess T, Andersson S G, Lupas A, Schaller M, Schäfer A, Kyme P, Martin J, Wälzlein J H, Ehehalt U, Lindroos H, Schirle M, Nordheim A, Autenrieth I B, Kempf V A: *Bartonella* adhesin A mediates a proangiogenic host cell response. J Exp Med 2004, 200:1267-1278
18. Conley T, Slater L, Hamilton K: *Rochalimaea* species stimulate human endothelial cell proliferation and migration in vitro. J Lab Clin Med 1994, 124:521-528
19. Palmari J, Teysseire N, Dussert C, Raoult D: Image cytology and topographical 1 analysis of proliferation of endothelial cells in vitro during *Bartonella* (*Rochalimaea*) infection. Analytical Cell Pathol 1996, 11:13-30
20. Maeno N H, Oda K, Yoshiie M R, Wahid T F, Matayoshi S: Live *Bartonella henselae* enhances endothelial cell proliferation without direct contact. Microb Pathog 1999,7 27:419-427
21. McCord A M, Cuevas J, Anderson B E: *Bartonella*-induced endothelial cell proliferation is mediated by release of calcium from intracellular stores. DNA Cell Biol 2007, 26:657-11 663
22. McCord A M, Burgess A W O, Whaley M J, Anderson B E: Interaction of *Bartonella henselae* with endothelial cells promotes monocyte/macrophage chemoattractant protein 1 gene expression and protein production and triggers monocyte migration. Infect Immun 2005, 73:5735-5742
23. Kempf V A, Volkmann B, Schaller M: Evidence of a leading role for VEGF in *Bartonella henselae*-induced endothelial cell proliferations. Cell Microbiol 2001, 3:623-632
24. Resto-Ruiz S I, Schmiederer M, Sweger D, Newton C, Klein T W, Friedman H, Anderson B E: Induction of a potential paracrine angiogenic loop between human THP-1 macrophages and human microvascular endothelial cells during *Bartonella henselae* infection. Infect Immun 2002, 70:4564-4570
25. Ferrara N, Gerber H P, Le Couter J: The biology of VEGF and its receptors. Nature Medicine 2003, 9:669-676
26. Schmid M C, Scheidegger F, Dehio M, Balmelle-Devaux N, Schulein R, Guye P, Chennakesava C S, Biedermann B, Dehio C: A translocated bacterial protein protects vascular endothelial cells from apoptosis. PLoS Pathog 2006, 2:1083-1096
27. Bizouarne N, Denis V, Legrand A, Monsigny M, Kieda C: A SV-40 immortalized murine endothelial cell line from peripheral lymph node high endothelium expresses a new alpha-1-fucose binding protein. Biol Cell 1993, 79:209-218
28. Bizouarne N, Mitterrand M, Monsigny M, Kieda C: Characterization of membrane sugar specific receptors in cultured high endothelial cells from mouse peripheral lymph nodes. Biol Cell 1993, 79:27-35
29. Kieda C, Paprocka M, Krawczenko A, Zalecki P, Dupuis P, Monsigny 1 M, Radzikowski C Dus D: New human microvascular endothelial cell lines with specific adhesion molecules phenotypes. Endothelium 2002, 9:247-261
30. Gurfield A N, Boulouis H J, Chomel B B, Kasten R W, Heller R, Bouillin C, Gandoin C, Thibault D, Chang C C, Barrat F, Piemont Y. Epidemiology of *Bartonella* infection in domestic cats in France. Vet Microbiol. 2001 May 21;80 (2):185-98
31. Fletcher N F, Brayden D J, Brankin B, Worrall S, Callanan J J Growth and characterisation of a cell culture model of the feline blood-brain barrier. Vet Immunol Immunopathol. 2006 Feb. 15;109(3-4):233-44.

The invention claimed is:

1. An isolated organ-specific feline endothelial cell comprising the Von Willebrand factor, the angiotensin converting enzyme and the clusters of differentiation (CD) 31, 34, 105, 54, 62E, 62P, and 146,
   wherein the isolated cell is selected from the cells deposited at the Collection Nationale de Culture de Microorganismes (CNCM), under the CNCM numbers No. I-4250 (F Int MEC), No. I-4251 (F PLN MEC), No. I-4252 (FUm EC), No. I-4253 (F Li MEC), No. I-4254 (F Sk MEC), No. I-4255 (F PP MEC), No. I-4256 (F He MEC), No. I-4257 (F Br MEC), No. I-4258 (F Lu MEC).

2. A cell culture comprising an isolated cell according to claim 1.

3. A cell culture comprising an isolated cell according to claim 1.

\* \* \* \* \*